US012594236B2

(12) United States Patent
Gutierro Aduriz et al.

(10) Patent No.: US 12,594,236 B2
(45) Date of Patent: *Apr. 7, 2026

(54) METHOD OF TREATING ACUTE EXACERBATION OF SCHIZOPHRENIA WITH LONG-ACTING INJECTABLE DEPOT COMPOSITION

(71) Applicant: LABORATORIOS FARMACEUTICOS ROVI, S.A., Madrid (ES)

(72) Inventors: Ibon Gutierro Aduriz, Madrid (ES); Guillermo Franco Rodriguez, Madrid (ES)

(73) Assignee: LABORATORIOS FARMACEUTICOS ROVI, S.A., Madrid (ES)

( * ) Notice: Subject to any disclaimer, the term of this patent is extended or adjusted under 35 U.S.C. 154(b) by 995 days.

This patent is subject to a terminal disclaimer.

(21) Appl. No.: 17/747,422

(22) Filed: May 18, 2022

(65) Prior Publication Data

US 2023/0029399 A1 Jan. 26, 2023

Related U.S. Application Data

(63) Continuation-in-part of application No. 17/377,640, filed on Jul. 16, 2021, now Pat. No. 12,318,387.

(51) Int. Cl.
| | |
|---|---|
| *A61K 31/519* | (2006.01) |
| *A61K 9/00* | (2006.01) |
| *A61K 47/20* | (2006.01) |
| *A61K 47/34* | (2017.01) |
| *A61P 25/18* | (2006.01) |

(52) U.S. Cl.
CPC .......... *A61K 9/0024* (2013.01); *A61K 31/519* (2013.01); *A61K 47/20* (2013.01); *A61K 47/34* (2013.01); *A61P 25/18* (2018.01)

(58) Field of Classification Search
CPC .. A61K 31/519; A61K 9/0019; A61K 9/0024; A61K 47/20; A61K 47/34; A61K 24/20; A61K 24/34; A61P 25/18
See application file for complete search history.

(56) References Cited

U.S. PATENT DOCUMENTS

| | | | |
|---|---|---|---|
| 3,636,956 A | 1/1972 | Schneider |
| 3,773,919 A | 11/1973 | Boswell |
| 4,389,330 A | 6/1983 | Tice |
| 4,523,591 A | 6/1985 | Kaplan |
| 4,530,840 A | 7/1985 | Tice |
| 4,938,763 A | 7/1990 | Dunn |
| 5,620,700 A | 4/1997 | Berggren |
| 5,688,801 A | 11/1997 | Mesens |
| 5,770,231 A | 6/1998 | Mesens |
| 6,143,314 A | 11/2000 | Chandrashekar |
| 6,194,006 B1 | 2/2001 | Lyons et al. |
| 6,331,311 B1 | 12/2001 | Brodbeck |
| 6,379,703 B1 | 4/2002 | Lyons et al. |
| 6,565,080 B1 | 5/2003 | Dunn |
| 6,565,874 B1 | 5/2003 | Dunn |
| 6,596,316 B2 | 7/2003 | Lyons et al. |
| 6,630,155 B1 | 10/2003 | Chandrashekar |
| 6,673,767 B1 | 1/2004 | Brodbeck |
| 6,773,714 B2 | 8/2004 | Dunn |
| 6,803,055 B2 | 10/2004 | Mesens |
| 7,118,763 B2 | 10/2006 | Mesens |
| 8,076,448 B2 | 12/2011 | Moore |
| 8,221,778 B2 | 7/2012 | Siegel |
| 8,324,343 B2 | 12/2012 | Moore |
| 9,180,197 B2 | 11/2015 | Dadey |
| 9,186,413 B2 | 11/2015 | Dadey |
| 9,597,402 B2 | 3/2017 | Luk et al. |
| 10,010,612 B2 | 7/2018 | Dadey et al. |
| 10,058,504 B2 | 8/2018 | Gutierro Aduriz et al. |
| 10,058,554 B2 | 8/2018 | Luk et al. |
| 10,085,936 B2 | 10/2018 | Gutierro Aduriz et al. |
| 10,182,982 B2 | 1/2019 | Gutierro Aduriz et al. |

(Continued)

FOREIGN PATENT DOCUMENTS

| | | |
|---|---|---|
| EP | 2394663 A1 | 12/2011 |
| EP | 2394664 A1 | 12/2011 |

(Continued)

OTHER PUBLICATIONS

Clark et al., CNS Drugs, vol. 34, pp. 841-852, publ. May 27, 2020 (Year: 2020).*

Kawata et al., Qual. Life Res., vol. 17, pp. 1247-1256, publ. 2008 (Year: 2008).*

Yapar et al. ("Effects of solvent combinations on drug release from injectable phase sensitive liquid implants", in Turk. J. Pharm. Sci. (2010), 7(1), 49-56).

Prashanth et a. ("Formulation and characterization of in situ implant of octeotride acetate", in Int. J. Pharm. (2013), 3(3), 565-573).

Calis et al. ("Influence of irradiation sterilization on poly(lactide-co-glycolide) microspheres containing anti-inflammatory drugs", in Il Farmaco (2002), 57, 55-62).

(Continued)

*Primary Examiner* — Sarah Pihonak
(74) *Attorney, Agent, or Firm* — Innovar, L.L.C.; Rick Matos

(57) ABSTRACT

A method of treating an episode of acute exacerbation of schizophrenia by intramuscular administration of a long-acting injectable depot composition containing risperidone is provided. The method provides a substantial reduction in PANSS (both positive and negative scales) and CGI-S scores within about eight days after administration of the composition and for up to at least four weeks. The method is used to treat a subject suffering a first-time episode of or a relapse of severe to moderate symptoms associated with schizophrenia. The method does not require loading doses of risperidone in the depot composition and does not require supplementation with oral risperidone after administration of the depot composition.

23 Claims, 6 Drawing Sheets

(56)  References Cited

U.S. PATENT DOCUMENTS

| | | | |
|---|---|---|---|
| 10,195,138 B2 | 2/2019 | Gutierro Aduriz et al. | |
| 10,335,366 B2 | 7/2019 | Gutierro Aduriz et al. | |
| 10,350,159 B2 | 7/2019 | Gutierro Aduriz et al. | |
| 10,376,590 B2 | 8/2019 | Dadey et al. | |
| 10,406,160 B2 | 9/2019 | Luk et al. | |
| 10,463,607 B2 | 11/2019 | Gutierro Aduriz et al. | |
| 10,881,605 B2 | 1/2021 | Gutierro Aduriz et al. | |
| 11,007,139 B2 | 5/2021 | Gutierro Aduriz et al. | |
| 11,013,683 B2 | 5/2021 | Gutierro Aduriz et al. | |
| 2002/0023409 A1 | 2/2002 | Py | |
| 2003/0165571 A1 | 9/2003 | Mesens | |
| 2004/0010224 A1 | 1/2004 | Bodmeier | |
| 2004/0247870 A1 | 12/2004 | Brown | |
| 2005/0003007 A1 | 1/2005 | Boix | |
| 2005/0025828 A1 | 2/2005 | Mesens | |
| 2005/0042294 A1 | 2/2005 | Thanoo | |
| 2006/0121085 A1 | 6/2006 | Warren | |
| 2006/0210604 A1 | 9/2006 | Dadey | |
| 2007/0003596 A1 | 1/2007 | Tittelbach | |
| 2007/0077304 A1 | 4/2007 | Luk | |
| 2008/0287464 A1 | 11/2008 | Wright | |
| 2009/0264491 A1 | 10/2009 | Mckay | |
| 2009/0305957 A1 | 12/2009 | Moore | |
| 2010/0015195 A1 | 1/2010 | Jain et al. | |
| 2010/0021544 A1 | 1/2010 | Bourges | |
| 2010/0266655 A1 | 10/2010 | Dadey | |
| 2010/0292195 A1 | 11/2010 | Dadey | |
| 2012/0108511 A1 | 5/2012 | Moore | |
| 2013/0171202 A1 | 7/2013 | Gutierro Aduriz et al. | |
| 2013/0177603 A1 | 7/2013 | Gutierro Aduriz et al. | |
| 2015/0147398 A1 | 5/2015 | Gutierro Aduriz et al. | |
| 2015/0150791 A1 | 6/2015 | Gutierro Aduriz et al. | |
| 2015/0196485 A1 | 7/2015 | Aduriz et al. | |
| 2018/0221272 A1 | 8/2018 | Gutierro Aduriz et al. | |
| 2018/0318208 A1 | 11/2018 | Gutierro Aduriz et al. | |
| 2019/0117554 A1 | 4/2019 | Gutierro Aduriz et al. | |
| 2019/0151230 A1 | 5/2019 | Gutierro Aduriz et al. | |
| 2019/0231682 A1 | 8/2019 | Franco Rodriguez et al. | |
| 2019/0254960 A1 | 8/2019 | Gutierro Aduriz et al. | |
| 2019/0321286 A1 | 10/2019 | Gutierro Aduriz et al. | |
| 2019/0328654 A1 | 10/2019 | Gutierro Aduriz et al. | |
| 2019/0365643 A1 | 12/2019 | Franco Rodriguez et al. | |
| 2020/0085728 A1 | 3/2020 | Gutierro Aduriz et al. | |
| 2021/0077380 A1 | 3/2021 | Gutierro Aduriz et al. | |
| 2021/0169778 A1 | 6/2021 | Franco Rodriguez et al. | |

FOREIGN PATENT DOCUMENTS

| | | | | | |
|---|---|---|---|---|---|
| EP | 2529756 | A2 | 12/2012 | | |
| EP | 2529757 | A1 | 12/2012 | | |
| WO | 95/29664 | A1 | 11/1995 | | |
| WO | 99/36071 | A1 | 7/1999 | | |
| WO | 2000040221 | A1 | 7/2000 | | |
| WO | 2001035929 | A2 | 5/2001 | | |
| WO | 02/38185 | A2 | 5/2002 | | |
| WO | 2002038185 | A2 | 5/2002 | | |
| WO | 2004/011054 | A2 | 2/2004 | | |
| WO | 2000024374 | A1 | 5/2004 | | |
| WO | 2004081196 | A2 | 9/2004 | | |
| WO | 2007/041410 | A1 | 4/2007 | | |
| WO | 2008059058 | A1 | 5/2008 | | |
| WO | 2008100576 | A2 | 8/2008 | | |
| WO | 2008/153611 | A1 | 12/2008 | | |
| WO | 2009/060473 | A2 | 5/2009 | | |
| WO | 2010/018159 | A1 | 2/2010 | | |
| WO | 2011042453 | A1 | 4/2011 | | |
| WO | 2011/151356 | A3 | 12/2011 | | |
| WO | 2011151355 | A1 | 12/2011 | | |
| WO | 2011151356 | A1 | 12/2011 | | |
| WO | 2013178811 | A1 | 12/2013 | | |
| WO | 2013178812 | A1 | 12/2013 | | |
| WO | 2014/019972 | A1 | 2/2014 | | |
| WO | WO-2020154315 | A1 * | 7/2020 | .......... | A61K 31/519 |

OTHER PUBLICATIONS

Indivior Inc. (Perseris package insert; NDA 210655; Jul. 27, 2018).

Janssen Pharmaceuticals (Risperdal Consta package insert; NDA 021346; Oct. 29, 2003).

Correll et al. ("Efficacy and Safety of once-monthly Risperidone ISM in schizophrenic patients with an acute exacerbation" in NPJ Schizophrenia (Nov. 25, 2020), 6:37).

Edison Investment Research Limited ("Doria Phase III Trial hits primary endpoint" Laboratorios Farmaceuticos ROVI, S.A. Mar. 19, 2019, at https://www.edisongroup.com/publication/doria-phase-iii-trial-hits-primary-endpoint/23705/).

Anta et al. ("Newer formulations of risperidone: remarks about Risperidone ISM" in CNS Drugs (Sep. 5, 2020); https://doi.org/10.1007/s40263-020-00762-0).

ROVI Pharmaceutical Laboratories ("Pharmacokinetics and Tolerability Study of Risperidone ISM in Schizophrenia (PRISMA-2)" NCT02086786 at https://clinicaltrials.gov/ct2/show/NCT02086786?term=NCT02086786&draw=2&rank=1; 2014).

ROVI Pharmaceutical Laboratories ("Study to evaluate the efficacy and safety of Risperidone ISM in Patients with Acute Schizophrenia (PRISMA-3)" NCT03160521 at https://clinicaltrials.gov/ct2/show/NCT03160521?term=NCT03160521&draw=2&rank=1, 2017).

ROVI Pharmaceutical Laboratories (Pharmacokinetic, Safety and Tolerability Study of Risperidone ISM and Different Dose Strengths (PRISMA-1), NCT01788774 at https://clinicaltrials.gov/ct2/show/NCT01788774?term=NCT01788774&draw=2&rank=1, 2013).

ROVI Pharmaceutical Laboratories ("Pharmacokinetics, Safety and Tolerability Study of Single Dose Administration of Risperidone ISM" at https://clinicaltrials.gov/ct2/show/NCT01320410?term=NCT01320410&draw=2&rank=1, 2011).

ROVI Pharmaceutical Laboratories ("Study to Evaluate the Efficacy and Safety of Risperidone ISM in Patients with Acute Schizophrenia: open label extension (PRISMA-3_OLE)" at https://clinicaltrials.gov/ct2/show/NCT03870880?term=NCT03870880&draw=2&rank=1, 2019).

Resomer RG503 product literature (2012) (http://www.resomer.com/product/biodegradable-polymers/Specifications/evonik-specification-resomer-rg-503.pdf).

Resomer RG504 product literature (2012) (http://www.resomer.com/product/biodegradable-polymers/Specifications/evonik-specification-resomer-rg-504.pdf).

Resomer RG752S product literature (2012) (http://www.resomer.com/product/biodegradable-polymers/Specifications/evonik-specification-resomer-rg-752-s.pdf).

Resomer RG753S product literature (2012) (http://www.resomer.com/product/biodegradable-polymers/Specifications/evonik-specification-resomer-rg-753-s.pdf).

Resomer products sheet of EVONIK (2012) (http://www.resomer.com/product/biodegradable-polymers/en/pharma-polymers/products/pages/bioresorbable-polymer.aspx#Controlled release).

Wang et al. ("Design of a long-term antipsychotic in situ forming implant and its release control method and mechanism", Int. J. Pharm., May 10, 2012;427(2):284-92.

Maryott et al. (Table of Dielectric Constants of Pure Liquids, National Bureau of Standards, Circular No. 514, Aug. 10, 1951).

Gouw et al. (Physical Properties of Triglycerides IV. Dielectric Constant, Fette Seifen Anstrichmittel, (1967), 69(4), 223-226).

LIDE (Properties of Common Laboratory Solvents, CRC Handbook of Chemistry and Physics 84th Ed., 2003-2004, Sect. 15-14, CRC Press, New York).

Citrome ("Sustained-release risperidone via subcutaneous injection: A systematic review of RBP-7000 (PERSERIS) for the treatment of schizophrenia" in Clinical Schizo. Related Psych., (2018), 130-141).

Bai et al. ("A comparative efficacy and safety study of long-acting risperidone injection and risperidone oral tablets among hospitalized patients: 12-week, randomized, single blind study" in Pharmacopsych. (2006), 39, 135-141).

Andom et al. ("Monthly extended release risperidone (RBP-7000) in the treatment of schizophrenia" in J. Clin. Psychopharm., (2019), 39(5), 428-433).

(56)          References Cited

OTHER PUBLICATIONS

European Medicines Agency ("Guideline on clinical investigation of medicinal products, including depot preparations in the treatment of schizophrenia" in EMA/CHMP/40072/2010 Rev. 1, (2012)).

Southern Health NHS Foundation Trust ( "Antipsychotic Guidelines Version 8" in SH CP 111, Feb. 2021).

Sussex Partnership NHS Foundation Trust ("Guidelines for the administration of long acting antipsychotic injections in adults" at www.sussexpartnership.nhs.uk/sites/default/files/documents/antipsychotic_guidelines_v4_apr_2018_-final_3_1.pdf, (2018)).

German Society for Psychiatry and Psychotherapy, Psychosomatic Medicine and Neurology ("S3 Guideline Schizophrenia" (AWMF register No. 038-009, Mar. 13, 2019).

National Institute for Health and Care Excellence ("NICE Guideline for Psychosis and Schizophrenia in adults: prevention and management" at www.nice.org.uk/guidance/cg178; 2014).

Gandara et al. ("Experience with injectable long-acting risperidone in long-term therapy after an acute episode of schizophrenia: the SPHERE study" in Expert Rev. Neurother. (2009), 9(10), 1463-1474).

Gopal et al. ("A post-hoc comparison of paliperidone palmitate to oral risperidone during initiation of long-acting risperidone injection in patients with acute Schizophrenia" in Innov. Clin. Neurosci. (2011), 8(8), 26-33).

Nasser et al. ("Efficacy, safety and tolerability of RBP-7000 once-monthly risperidone for the treatment of acute schizophrenia: an 8-week, randomized, double-blind, placebo-controlled, multicenter Phase 3 study" in J. Clin. Psycopharm. (2016), 36(2), 130-140).

\* cited by examiner

Placebo          LAI depot composition

METHOD OF TREATING ACUTE EXACERBATION OF SCHIZOPHRENIA WITH LONG-ACTING INJECTABLE DEPOT COMPOSITION

CROSS-REFERENCE TO EARLIER FILED APPLICATION

The present application claims the benefit of and is a continuation-in-part of application Ser. No. 17/377,640, filed Jul. 16, 2021, the entire disclosure of which is hereby incorporated by reference.

FIELD OF THE INVENTION

The present invention relates to use of a long-acting injectable (LAI) depot composition comprising risperidone for treating psychotic disorders, in particular acute exacerbation of schizophrenia. The method provides for intramuscular administration of the composition once approximately every 28 days (or approximately once-monthly), does not require prior administration of risperidone loading dose(s) of said LAI depot composition, and does not require concomitant administration of the LAI depot composition and oral supplementation with risperidone. The composition provides a therapeutically effective plasma concentration of risperidone from the first day of administration (within 8 to 24 hours after administration) throughout a period of at least about 28-31 days or more. The composition provides improved performance over other LAI depot compositions, in particular for the treatment of acute episodes of psychosis, e.g. acute exacerbation of schizophrenia. Treatment of first time and recurrent acute episodes is within the scope of the invention.

BACKGROUND OF THE INVENTION

Schizophrenia may occur in various levels of intensity. Many patients with these mental illnesses achieve symptom stability with available oral antipsychotic medications; however, it is estimated that up to 75% have difficulty adhering to a daily oral treatment regimen, i.e. compliance problems. Problems with adherence often result in worsening of symptoms, suboptimal treatment response, frequent relapses and re-hospitalizations, and an inability to benefit from rehabilitative and psychosocial therapies. From a social and public health perspective, schizophrenia is one of the leading causes of disability associated to mental disorders and patients are burdened by a high rate of comorbidities and by a progressive decline in social functioning. Despite the fact that the heterogeneity of schizophrenia in terms of symptoms severity, social and occupational functioning are typically affected, in the light of this, the evaluation of quality of life is relevant since the illness interacts with contextual factors (social and environmental), even more than somatic illnesses. Hence, improving quality of life (QoL) in schizophrenia is a cornerstone for shifting toward a person-centered and recovery-oriented care. Both positive and negative symptomatology influence the quality of life, especially negative symptoms, even if a clear separation between primary and secondary negative symptoms has not been considered. A previous study (Montemagni et al, "Second-generation long-acting injectable antipsychotics in schizophrenia: patient functions and quality of life" in Neuropsyc. Dis. Treat. (2016), 12, 917-929) using Risperidone LAI, conducted on several patient profiles (stable, unstable, hospitalized), and with different design (RCTs, open labels, observational, switching studies), demonstrated an overall positive outcome regarding schizophrenia patients functioning and QoL in stable patients but not in unstable patients. Kaplan et al. ("Impact of long-acting injectable antipsychotics on medication adherence and clinical, functional, and economic outcomes of schizophrenia" in Patient Pref. Adher. (2013), 7, 1171-1180) report that some LAI antipsychotics provide improved clinical outcomes when compared to placebo but not when compared to oral antipsychotics. It would be a significant improvement over the art to provide a risperidone LAI that provides such benefits in both stable and unstable patients.

Risperidone, and its primary active metabolite 9-OH-risperidone (paliperidone), are indicated for the treatment of psychotic disorders such as schizophrenia, schizoaffective disorder, bipolar disorder, and bipolar mania. Risperidone can be administered orally in commercially available tablet, solution, or orally disintegrating tablet dosage forms.

Numerous publications discuss the proper use of oral risperidone versus LAI's containing risperidone for the treatment of the various grades of schizophrenia. Citrome (Clinical Schizo. Related Psych., (2018), 130-141), Bai et al. (Pharmacopsych. (2006), 39, 135-141), and Andorn et al. (J. Clin. Psychopharm., (2019), 39(5), 428-433). Patients with schizophrenia suffering a relapse need urgent attention owing to the severity of the symptomatology and future consequences if not treated immediately.

To date, the most widely accepted treatment protocol for an episode of acute exacerbation of schizophrenia is daily administration of oral risperidone until resolution of the episode. The patient may then continue to receive risperidone orally or may receive LAI depot composition of risperidone.

The European Medicines Agency published its "Guideline on clinical investigation of medicinal products, including depot preparations in the treatment of schizophrenia" (EMA/CHMP/40072/2010 Rev. 1, (2012)) stating, "Depot preparations are meant for maintenance treatment, once a patient is stabilized satisfactorily on an oral preparation . . . Depot preparations of antipsychotic products will usually be given after the patient is stabilized on the oral form."

Southern Health NHS Foundation Trust published its "Antipsychotic Guidelines Version 8" (SH CP 111, February 2021). They specifically recommend use of LAIs only for maintenance treatment. Sussex Partnership NHS Foundation Trust published its "Guidelines for the administration of long acting antipsychotic injections in adults" (www.sussexpartnership.nhs.uk/sites/default/files/documents/antipsychotic_guidelines_v4_-_apr_2018_-_final_3_1.pdf, (2018)). They specifically state "Long acting antipsychotic injections (LAAIs) are indicated for the maintenance treatment in the treatment of schizophrenia, mania, and other psychoses." They further caution, "With risperidone long acting injection (RISPERDAL CONSTA) blood levels drop rapidly shortly after the due day so the likelihood of relapse if not administered on or soon after the due date is greater." With regard to mode of administration, they discourage subcutaneous administration into fatty tissue as is required for the product PERSERIS due to the significant delay in systemic absorption of drug injected into the fatty tissue.

The German Society for Psychiatry and Psychotherapy, Psychosomatic Medicine and Neurology published it "S3 Guideline Schizophrenia" (AWMF register No. 038-009, Mar. 13, 2019). They state that there is insufficient evidence to prove that intramuscular or intravenous administration of antipsychotics are efficacious in treating acute disease. They also include a table (14), wherein they indicate that LAI risperidone is not recommended for treatment of acute states of psychoses.

The National Institute for Health and Care Excellence published its NICE Guideline for Psychosis and Schizophrenia in adults: prevention and management (2014, www.nice.org.uk/guidance/cg178). They state that the proper "treatment options for people with an acute exacerbation or recurrence of psychosis or schizophrenia" should be "oral antipsychotic medication in conjunction with psychological interventions". They only recommend offering LAI antipsychotic "after an acute episode".

LAI depot compositions are known: U.S. Pat. No. 8,221,778 to Siegel et al. (corresponding to WO 2005/070332), U.S. Pat. Nos. 5,688,801, 6,803,055, 5,770,231, 7,118,763, 4,389,330 to Dunn, U.S. Pat. Nos. 4,530,840, 6,673,767 to Brodebeck, U.S. Pat. No. 6,143,314 to Chandrashekar, WO 2004/081196, WO 2001/035929, WO 2008/153611 A2 to QLT USA, WO 2000/024374, WO 2002/038185, WO 2008/100576, WO 2011/151355 A1 to Laboratorios Farmaceuticos ROVI, S.A., WO 2011/42453, U.S. Ser. No. 10/085,936 to Gutierro Aduriz, U.S. Ser. No. 10/463,607 to Gutierro Aduriz, U.S. Ser. No. 10/182,982 to Gutierro Aduriz, US 2020/0085728 A1 to Gutierro Aduriz, EP 2394664 A1 to Laboratorios Farmaceuticos ROVI, S.A., WO 2011/151355 A1 to Laboratorios Farmaceuticos ROVI, S.A., U.S. Ser. No. 10/058,504 Gutierro Aduriz, U.S. Ser. No. 10/881,605 Gutierro Aduriz, U.S. Ser. No. 10/195,138 Gutierro Aduriz, US 2021/0077380 A1 to Laboratorios Farmaceuticos ROVI, S.A., EP 2394663 A1 to Laboratorios Farmaceuticos ROVI, S.A., WO 2011/151356 A2 to Laboratorios Farmaceuticos ROVI, S.A., U.S. Ser. No. 10/350,159 to Gutierro Aduriz, US 2019/0328654 A1 to Laboratorios Farmaceuticos ROVI, S.A., EP 2529757 A1 to Laboratorios Farmaceuticos ROVI, S.A., WO 2013/178811 A1 to Laboratorios Farmaceuticos ROVI, S.A., U.S. Ser. No. 10/335,366 to Gutierro Aduriz, US 2019/0254960 A1 to Laboratorios Farmaceuticos ROVI, S.A., U.S. Ser. No. 11/007,139 to Gutierro Aduriz, EP 2529756 A2 to Laboratorios Farmaceuticos ROVI, S.A., WO 2013/178812 A1 to Laboratorios Farmaceuticos ROVI, S.A., US 2008/0287464 A1 to Wright, US 2009/0264491 A1 to McKay, US 2004/0010224 A1 to Bodmeier, US 2007/0077304 A1 to Luk, US 2010/0015195 A1 to Jain, US 2010/0266655 A1 to Dadey, WO 95/29664 to Alkermes, WO 2004/011054 A2 to Alza, WO 2007/041410 A2 to Luk, WO 2008/059058 A1 to Bourges, WO 2010/018159 A1 to Schoenhammer.

Two such LAI products containing risperidone have been approved by the U.S. F.D.A.

RISPERDAL CONSTA® (NDA N021346; dosage strengths-12.5 mg/vial, 25 mg/vial, 37.5 mg/vial and 50 mg/vial; U.S. Pat. Nos. 6,596,316, 6,379,703, 6,194,006, WO 2000/40221) is an intramuscular risperidone-containing PLGA microparticle formulation, and it is intended to deliver therapeutic levels of risperidone suitable for bi-weekly administration. However, due to the inherent lag phase of most microparticle-based products, the patient is required to supplement the first weeks with daily doses of oral risperidone after first administration. Approximately three weeks after a single intramuscular injection of RISPERDAL CONSTA® and concurrent daily doses of oral risperidone, the microspheres release sufficient risperidone in the systemic circulation that the patient can discontinue supplementation with daily doses of the oral therapy. However, this period of oral supplementation could be a risk factor of non-compliance. Also, the presence in the body of two doses at the same time could present a potential risk of adverse events, such as irregular formulation behavior and toxicity.

Gándara et al. report on the results of a clinical study evaluating RISPERDAL CONSTA ("Experience with injectable long-acting risperidone in long-term therapy after an acute episode of schizophrenia: the SPHERE study" in Expert Rev. Neurother. (2009), 9(10), 1463-1474). They found that treatment of acute episode of schizophrenia required concomitant oral supplementation with risperidone or another antipsychotic during the first three weeks after initiation of LAI therapy, meaning that two doses of the LAI were required along with daily doses of oral risperidone in order to treat the acute episodes.

Gopal et al. ("A post-hoc comparison of paliperidone palmitate to oral risperidone during initiation of long-acting risperidone injection in patients with acute Schizophrenia" in Innov. Clin. Neurosci. (2011), 8(8), 26-33) indicate that treatment of acute episodes with the LAI depot composition RISPERDAL CONSTA requires oral risperidone supplementation for at least three weeks following initiation of therapy with the LAI.

Based upon the above clinical findings and clinician recommendations, RISPERDAL CONSTA is not suitable on its own for treating an episode of acute exacerbation of schizophrenia.

PERSERIS® (NDA N210655; dosage strengths-90 mg and 120 mg per dose; U.S. Pat. Nos. 9,180,197, 9,186,413, 9,597,402, U.S. Ser. No. 10/010,612, U.S. Ser. No. 10/058,554, U.S. Ser. No. 10/376,590, U.S. Ser. No. 10/406,160) is a microparticulate risperidone-containing depot formulation intended for subcutaneous administration in adipose (fatty) tissue. Nasser et al. ("Efficacy, safety and tolerability of RBP-7000 once-monthly risperidone for the treatment of acute schizophrenia: an 8-week, randomized, double-blind, placebo-controlled, multicenter Phase 3 study" in J. Clin. Psycopharm. (2016), 36(2), 130-140) evaluated the RBP-7000 LAI (90 mg and 120 mg dosage strengths) for treating acute schizophrenia. They reported, "RBP-7000 produced statistically and clinically significant differences in mean reductions from baseline in PANSS total scores (90-mg RBP-7000 compared with placebo, −6.148 (−9.982 to −2.314), P=0.0004; 120-mg RBP-7000 compared with placebo, −7.237 (−11.045 to −3.429), P<0.0001) and significantly improved Clinical Global Impression-Severity scores (CGIS; 90-mg RBP-7000 compared with placebo, −0.350 (−0.557 to −0.143), P=0.0002; 120-mg RBP-7000 compared with placebo, −0.396 (−0.602 to −0.190), P<0.0001)." Importantly, Nasser report that the improvement for PANSS was primarily only in the positive subscale, but there was no statistically significant improvement in the negative subscale. They found, "The change from baseline in PANSS negative scale scores, however, was not significantly different across the treatment and placebo groups. These results are consistent with previous reports regarding the efficacy of risperidone in schizophrenia." They also found, "The onset of significant improvement in PANSS total score and CGI-S scores occurred by day 15 and was maintained until the end of the study." Additionally, subcutaneous administration leads to potential higher variability due to higher temperature fluctuation of the subcutaneous tissue, and a lower bioavailability of risperidone is achieved due to subcutaneous administration.

Another LAI product containing risperidone is still undergoing clinical evaluation for the treatment of schizophrenia: Correll et al. (NPJ Schizophrenia (Nov. 25, 2020), 6:37), Edison Investment Research Limited ("Doria Phase III Trial hits primary endpoint, Laboratorios Farmaceuticos ROVI, S.A. Mar. 19, 2019, www.edisongroup.com/publication/doria-phase-iii-trial-hits-primary-endpoint/23705/), NCT02086786, NCT03160521, NCT01788774, NCT01320410, NCT03870880, NCT03160521, NCT01788774, and Anta et al. (Newer formulations of risperidone: remarks about Risperidone ISM" in CNS Drugs (Sep. 5, 2020; doi.org/10.1007/s40263-020-00762-0). The composition of the product is not disclosed in those publications.

U.S. Pat. No. 6,331,311 issued to Brodbeck also discloses injectable depot compositions comprising a biocompatible polymer such as PLGA, a solvent such as N-methyl-2-pyrrolidone and a beneficial agent such as a drug, further comprising an emulsifying agent such as polyols. However, the compositions disclosed do not perform satisfactorily when the beneficial agent is risperidone because the use of a two-phase composition with emulsifying agents accelerates implant hydration and increases effective releasing surface area, impairing the control on the initial burst release and originating a fast decrease in drug release from the first days to the following ones. For example, a comparator composition was prepared according to the '311 Patent. A container containing risperidone (150 mg), PLGA (300 mg, having an inherent viscosity of 0.32 dl/g and irradiated by β-irradiation to a dose of 25 KGy) and NMP (700 mg) was prepared. Another container containing polyvinyl alcohol in water (1 ml of a 2% wt/v). The contents of the containers were mixed, then the mixture was transferred to a syringe and injected intramuscularly (an amount equivalent to 2.5 mg risperidone) into the gluteus of New Zealand White rabbits (n=3). More than 70% of the total AUC of active moiety was released within the first 5 days after the injection. Such a formulation is unable to provide therapeutic plasma levels of risperidone for a period of at least four weeks.

U.S. Pat. No. 4,938,763, issued to Dunn et al., discloses a method for an injectable in situ forming implant. A biodegradable polymer or copolymer dissolved in a water-miscible solvent with a biologically active agent either is dissolved or dispersed within the polymeric solution. Once the polymeric solution is exposed to body fluids, the solvent diffuses and the polymer solidifies thereby entrapping the drug within the polymer matrix. Even though Dunn et al. discloses the use of water miscible solvents for obtaining in situ forming polymeric implants, it discloses a number of polymers and solvents and even proportions between the different ingredients that do not produce a satisfactory implant with the appropriate release characteristics, particularly when the implant contains risperidone as active principle. For example, a comparator composition was prepared according to the '763 Patent. A container containing risperidone (50 mg) and PLGA (784 mg, monomer ratio of lactic acid to glycolic acid monomer of 75:25 and having an inherent viscosity of 0.20 dl/g) was prepared. Another container containing NMP (1666 mg) was prepared. The contents of the containers were mixed. Then the mixture was transferred to a syringe and a portion (1250 mg, corresponding to 25 mg of risperidone) was injected into an aqueous liquid to determine its in vitro release profile. More than 50% of the risperidone was released within the first 2 days. Such a formulation is unable to provide therapeutic plasma levels of risperidone for a period of at least four weeks.

A need remains in the art for improved methods of treating episodes, whether first time or recurring, of acute exacerbation of schizophrenia. It would be a significant advance in the art to provide an improved method of treating acute exacerbation of schizophrenia with a LAI depot composition comprising risperidone as first line therapy, wherein the method would not require oral risperidone supplementation or risperidone loading dose(s) of said LAI depot composition, and wherein the composition would provide therapeutically effective plasma levels of risperidone within 8 to 24 hours after administration and would provide efficacious treatment of the acute episode within about 8 days or within about 15 days after administration. It would be a further improvement in the art to provide a method requiring a reduced dose of risperidone in a LAI depot composition for treating acute exacerbation of schizophrenia, because a reduced dose would result in a lower incidence of drug-related adverse events (side effects) as compared to other known LAI depot compositions of risperidone on a dose equivalent basis.

SUMMARY OF THE INVENTION

The present invention seeks to provide an improved method of treating an episode of acute psychosis, such as acute exacerbation of schizophrenia, by intramuscular administration about once every about 28 days of a LAI depot composition comprising risperidone. The invention also provides a method of improving the quality of life of a subject suffering from schizophrenia. The invention also provides a method of improving the quality of life of a subject suffering from schizophrenia.

As compared to the use of other LAI depot compositions containing risperidone, the method of the invention a) more rapidly achieves and maintains plasma concentration of active moiety (of risperidone and its metabolite 9-OH-risperidone, if present) in the therapeutic range; b) provides a faster reduction ins PANSS; c) reduces the PANSS and CGI symptoms in the subject (undergoing an episode of acute exacerbation) as rapidly as does treatment with oral doses of risperidone in immediate (or rapid) release tablets (e.g. RISPERDAL tablets); and d) provides a substantially improved clinical benefit (therapeutic result). The method of the invention also results in improved quality of life in a subject having schizophrenia.

Unlike the use of other LAI depot compositions containing risperidone, the method of the invention also provides the advantage that therapeutic plasma concentrations of active moiety can be maintained following termination of an oral dosing regimen of risperidone by administering the LAI depot composition as defined herein. Accordingly, the invention provides a method of switching a subject from a once-daily oral dosing regimen of risperidone to a once-every 28 days LAI depot composition dosing regimen of risperidone, the method comprising a) discontinuing once-daily oral administration of risperidone in a subject in need thereof; and b) within 24-48 hours or within 24 hours of said discontinuing, administering to said subject a LAI depot composition as described herein comprising a 75-100 mg or 25-150 mg dose of risperidone, thereby maintaining a therapeutically effective plasma concentration of active moiety in said subject for about 28 days. In some embodiments, wherein the subject has been receiving once-daily oral doses of less than 4 mg of risperidone, the subject is administered an amount of LAI depot composition, as described herein, comprising up to about 75 mg of risperidone. In other embodiments, wherein the subject has been receiving once-daily oral doses of 4 mg or more of risperidone, the subject is administered an amount of LAI depot composition, as described herein, comprising more than 75 mg and up to about 150 mg of risperidone, or comprising about 100 mg of risperidone.

Also, unlike the use of other LAI depot compositions containing risperidone, the method of the invention also provides the advantage that therapeutic plasma concentrations of active moiety can be maintained following termination of a LAI depot composition dosing regimen by orally administering once-daily doses of risperidone. Accordingly, the invention provides a method of switching a subject from a once-every 28-days LAI depot composition dosing regimen of risperidone to a once-daily oral dosing regimen of risperidone, the method comprising, within 0-5 days or within 0-two days of the end of a 28-day period following intramuscular administration of a LAI depot composition as described herein of risperidone, chronically orally administering once-daily doses of risperidone. In some embodiments, wherein the subject has been receiving once-every 28-day doses of up to 75 mg of risperidone in a LAI depot composition, as described herein, the subject is chronically administered once-daily oral doses of less than 4 mg of risperidone. In other embodiments, wherein the subject has been receiving once-every 28-day doses of more than 75 mg of risperidone (or about 100 mg of risperidone) in a LAI depot composition, as described herein, the subject is chronically administered once-daily oral doses of 4 mg or more of risperidone.

The invention also provides a method of switching a subject from an oral dosing protocol to a long-acting injectable (LAI) composition dosing protocol, the method comprising a) identifying a subject having a psychotic disorder and receiving less than 4 mg of oral risperidone daily; b) discontinuing said oral risperidone; and c) about every four weeks or about once-monthly intramuscularly administering to said subject an amount of LAI depot composition comprising about 75 mg of risperidone. In some embodiments, the first dose of LAI depot composition is administered within 24 to 48 h or within 24 h after said discontinuing.

The invention also provides a method of switching a subject from an oral dosing protocol to a long-acting injectable (LAI) depot composition dosing protocol, the method comprising a) identifying a subject having a psychotic disorder and receiving 4 mg or more of oral risperidone daily; b) discontinuing said oral risperidone; and c) about every four weeks or about once-monthly intramuscularly administering to said subject an amount of LAI depot composition comprising about 100 mg of risperidone. In some embodiments, the first dose of LAI depot composition is administered within 24 to 48 h or within 24 h after said discontinuing.

As compared to the use of other LAI depot compositions containing risperidone, the method of the invention also a) employs a lower dose of risperidone to achieve therapeutically relevant target endpoints (PANSS, CGIS), meaning the method of invention provides an improved dose-response as compared to other LAI depot composition based methods; b) employs a dosing regimen of intramuscular administration of 75-100 mg or 25-150 mg of risperidone once every about 28 days; c) achieves a substantially improved therapeutic result in terms of PANSS (both positive and negative subscales) and CGIS when compared to RISPERDAL CONSTA (as described in NDA N021346) and PERSERIS (as described in NDA N210655) on a dose equivalent basis; d) does not require loading doses of risperidone as does RISPERDAL CONSTA; e) does not require oral supplementation with risperidone as does RISPERDAL CONSTA; e) provides a therapeutically effective plasma concentration of risperidone from the first day of administration (within 2 to 24 hours or within 8 to 24 hours after administration) throughout a period of about 28-31 days or more, unlike RISPERDAL CONSTA and PERSERIS; and/or f) achieves substantially faster resolution of an episode of acute exacerbation of schizophrenia (as early as about 8 days after administration for the 100 mg dosage strength and as early as about 15 days for the 75 mg dosage strength) than RISPERDAL CONSTA and PERSERIS on a dose equivalent basis.

Aspects of the invention include those wherein the initial dose of LAI depot composition is the same strength as the maintenance dose of said LAI depot composition. For example, for a subject receiving an initial about 75 mg strength dose of risperidone in LAI depot composition, the second and subsequent maintenance doses of said composition will comprise an about 75 mg strength dose of risperidone in said composition. Likewise, for a subject receiving an initial about 100 mg strength dose of risperidone in LAI depot composition, the second and subsequent maintenance doses of said composition will comprise an about 100 mg strength dose of risperidone in said composition. Accordingly, the invention includes embodiments wherein the dosage strength of risperidone in LAI depot composition doses administered to a subject remain the same throughout a treatment period.

Alternatively, other aspects of the invention include those wherein the initial dose of LAI depot composition has a higher strength of risperidone than does the maintenance dose of said composition administered to the same subject. For example, for a subject receiving an initial about 100 mg strength dose of risperidone in LAI depot composition according to any of the methods described herein, the second and subsequent maintenance doses of said composition will comprise an about 75 mg strength dose of risperidone in said composition.

Aspects of the invention provide a method of treating an episode of acute exacerbation of schizophrenia in a human subject, the method comprising administering to a subject undergoing said episode a LAI depot composition comprising risperidone, wherein said composition is administered intramuscularly once about every 28 days or once monthly. Said LAI depot composition is a defined herein. The episode may be a first-time episode or one of plural recurring episodes.

In some embodiments, the intramuscular administration occurs within two weeks or less, within ten days or less, within one week or less, within five days or less, within three days or less, within two days or less, or within one day or less of occurrence of said episode of acute exacerbation of schizophrenia.

When practiced as described herein, the method of the invention results in reduced on-symptom days, reduced in-hospital days, and improved total PANSS as compared to methods of treatment employing RISPERDAL CONSTA and PERSERIS LAI depot compositions on a dose equivalent basis. The instant method also provides reduced total treatment-emergent adverse events (TEAEs) compared with RISPERDAL CONSTA and PERSERIS LAI depot compositions on a dose equivalent basis and, in a population of treated subjects, provides a lower rate of discontinuation due to TEAEs compared with placebo.

In some embodiments, prior to being administered the LAI depot composition, the subject a) is unstable and experiencing severe to moderate psychotic symptoms; b) is experiencing a first acute exacerbation of schizophrenia; c) is undergoing treatment with one or more oral antipsychotic drugs; d) has experienced prior episode(s) of acute exacerbation of schizophrenia; e) is experiencing worsening psychotic symptoms or impending relapse of psychosis; f) is experiencing a relapse of severe to moderate psychotic symptoms; and/or g) is undergoing treatment with a LAI depot composition not according to the invention.

In some embodiments, a) the composition comprises about 25 mg to about 150 mg, about 25 mg to about 125 mg, about 25 mg to about 100 mg, about 50 mg to about 150 mg, about 50 mg to about 125 mg, about 50 mg to about 100 mg, about 75 mg to about 150 mg, about 75 mg to about 125 mg, about 75 mg to about 100 mg, about 25 mg, about 50 mg, about 75 mg, about 100 mg, about 125 mg, or about 150 mg of risperidone; b) the composition comprises risperidone, DMSO, and PLGA copolymer; c) the LAI depot composition forms a biodegradable implant in muscle after administration; d) ≤2.5%, ≤5%, ≤7.5%, ≤10%, ≤20% of the risperidone is dissolved in said composition before administration; e) >0%, ≥4.5%, ≥1%, ≥5%, ≥10%, ≥15%, or up to about 20% wt of the risperidone is dissolved in said composition before administration; f) the PLGA copolymer has a monomer ratio of lactic acid to glycolic acid in the range from about 50:50 to about 75:25, about 35:65 to about 75:25, about 45:55 to about 70:30, about 50:50 to about 65:35, or about 65:35 to about 75:25, 45:55 to 55:45, or 48:52 to 52:48, or about 50:50, i.e. 50:50±10%, or 75:25±10%; g) before administration, a polymeric solution used to form the LAI depot composition has a viscosity in the range of about 0.5-7 Pa·s, about 0.5-4 Pa·s, about 0.7-4 Pa·s, about 0.5-3.0 Pa·s, about 0.7-3.0 Pa·s, about 1.5-2.1 Pa·s±10%, about 1.5 to about 2.5 Pa·s, about 1.5 to about 2.3 Pa·s, or about 1.7-1.8 Pa·s±10%; h) the PLGA copolymer has an inherent viscosity in the range of 0.20-0.60 dl/g, about 0.30-0.55 dl/g, about 0.36-0.52 dl/g, about 0.40-0.58 dl/g, or about 0.46-0.51 dl/g measured in chloroform at 30° C. and at a concentration of 0.5% wt with a Ubbelhode size 0B glass capillary viscometer; i) the LAI depot composition has a mass ratio of DMSO to risperidone of about 5:1 to about 4:1, about 4.6:1 to about 4.8:1, about 4.6:1 to about 4.7:1, about 4.67:1, about 4.66:1 or about 4.68:1, or about 4.66:1; j) the LAI depot composition has a mass ratio of risperidone to (PLGA+risperidone), expressed as the percentage of the risperidone weight with respect to total weight of the risperidone plus PLGA, in the range of about 15-40% weight, about 25-35% wt, about 30-35%, about 31-35%, about 32-34% or about 33% wt; k) the PLGA copolymer is end-capped with an ester group or a carboxyl group; l) the content of risperidone in the formulation is about 10-15% wt, about 11-14% wt, about 12-14% wt, or about 13% wt; m) the risperidone is partially dissolved or substantially completely undissolved in said composition; n) the PLGA polymer has been irradiated with beta or gamma radiation preferably in the range of 10-30 KGy, more preferably in the range of 15-30 Kgy, and most preferably between 16-25 Kgy±10%; o) the composition is sterile; p) the injectable composition continuously provides therapeutically effective plasma levels of drug in the subject throughout a dosing period of at least four weeks beginning from the day of administration; q) before administration, the LAI depot composition has a viscosity in the range of about 1.0-7.0 Pa·s, about 1.5-7.0 Pa·s, or about 1.8-6.5 Pa·s; r) the mass ratio of solvent (DMSO) to polymeric solution, expressed as the weight percentage of solvent with respect to the weight of polymer+solvent, is about 50-75%, about 65-75%, about 60-70%, about 68-72%, or about 70%; s) the concentration of LPGA in the LAI depot composition is in the range of 24%-50% wt, 24%-40% wt, 24%-30% wt, 25-27% wt or 26% wt, (expressed as the percentage of polymer weight based on total composition weight); and/or t) the content of DMSO in the injectable depot composition is about 55-65% wt, about 57-63% wt, about 60-62% wt, or about 61% wt based upon the total weight of the composition.

In some embodiments, the method a) excludes the step of administering one or more loading (plural) doses of risperidone in said LAI depot composition before said intramuscular administration of the LAI depot composition; and/or b) excludes the step of orally administering one or more doses of risperidone within said 28-day or monthly period.

Whereas other LAI depot compositions, such as PERSERIS, provide improvements in only the positive subscale of the PANSS, the method of invention unexpectedly provides improvements in both the positive and negative subscales of the PANSS and also provides improvements in the CGI-S. The method provides a faster resolution of the acute exacerbation as compared to RISPERDAL CONSTA and PERSERIS on a dose equivalent basis. When compared on a calculated dose equivalent basis to use of RISPERDAL CONSTA and PERSERIS, the method of the invention provides an improved dose-response in the treatment of acute exacerbation of schizophrenia.

The invention also provides a method of treating a subject suffering a relapse of psychosis, such as an episode of acute exacerbation of schizophrenia, the method comprising intramuscularly administering to a subject undergoing said episode a LAI depot composition comprising 25-150 mg of risperidone, DMSO, and PLGA copolymer, wherein after said administration an implant formed from said composition provides therapeutic plasma concentrations of risperidone and/or its metabolite (9-OH-risperidone, also known as paliperidone) within 2-24 hours after administration and continuously for a period of at least about 28 days, thereby providing significant reduction in symptoms associated with said psychosis (for example as determined by total PANSS (including the positive and negative scales) and CGI-S) starting from about 8 days after said administering, wherein said method excludes oral supplementation with risperidone and excludes administration of one or more (plural) loading doses of risperidone in said LAI depot composition.

In some embodiments, the invention provides a) significantly improved PANSS total score (mean difference, 95% CI) from baseline to day 85 of −13.0 (95% CI, −17.3 to −8.8) (p<0.0001) on a placebo-adjusted basis following administration of 75 mg of risperidone in a LAI depot composition of the invention; b) a) significantly improved PANSS total score (mean difference, 95% CI) from baseline to day 85 of −13.3 (−17.6 to −8.9) (p<0.0001) on a placebo-adjusted basis following administration of 100 mg of risperidone in a LAI depot composition of the invention; c) significantly improved CGI-S total score (mean difference, 95% CI) from baseline to day 85 of −0.7 (−1.0 to −0.5) (p<0.0001) on a placebo-adjusted basis following administration of 75 mg of risperidone in a LAI depot composition of the invention; and/or d) significantly improved CGI-S total score (mean difference, 95% CI) from baseline to day 85 of −0.7 (−1.0 to −0.5) (p<0.0001) on a placebo-adjusted basis following administration of 100 mg of risperidone in a LAI depot composition of the invention.

In some embodiments, the invention provides a method of treating an episode of acute exacerbation of schizophrenia, the method comprising intramuscularly administering to a subject undergoing said episode a LAI depot composition comprising 75-100 mg of risperidone, DMSO, and PLGA copolymer, wherein a) said composition is administered intramuscularly once about every 28 days or once monthly; b) after said administration, an implant formed from said composition provides therapeutic plasma concentrations of risperidone and/or its metabolite (9-0H-risperidone, also known as paliperidone) within 2-24 hours after administration and continuously for a period of at least about 28 days; c) after said administration, an implant formed from said composition provides a reduction of total PANSS score, in both the positive and negative scales, of −13.3 (−17.6 to −8.9) (p<0.0001) and a reduction of CGI-S total score of −0.7 (−1.0 to −0.5) (p<0.0001), said scores being on a placebo-adjusted basis.

The invention also provides a method of treating a subject suffering a relapse of psychosis, such as an episode of acute exacerbation of schizophrenia, the method comprising administering to a subject undergoing said episode a LAI depot composition comprising 25-150 mg of risperidone, DMSO, and PLGA copolymer, wherein a) said composition is administered intramuscularly once about every 28 days or once monthly; b) >0 wt % and 20% of said risperidone is dissolved in said composition prior to administration; c) the PLGA copolymer has a monomer ratio of lactic acid to glycolic acid in the range from about 50:50 to about 75:25; d) the LAI depot composition has a viscosity in the range of about 0.5-7 Pa·s; e) the LAI depot composition has a mass ratio of DMSO to risperidone of about 5:1 to about 4:1; and f) the LAI depot composition has a mass ratio of risperidone to (PLGA+risperidone), expressed as the percentage of the risperidone weight with respect to total weight of the risperidone plus PLGA, in the range of about 25-35% wt.

Another aspect of the invention provides a method of improving mental functioning and/or social integration in a human subject experiencing or having recently experienced an episode of acute exacerbation of schizophrenia, the method comprising administering to a subject undergoing said episode a long-acting injectable (LAI) depot composition comprising a maintenance dose of risperidone, wherein said composition is administered intramuscularly once about every 28 days or about once monthly, thereby improving mental functioning and/or social integration in said subject as measured using the patient-reported 20-items scale Subjective Well-Being Under Neuroleptics Treatment (SWN-20); and/or improving personal or social relationships, social useful activities, or reducing disturbing and aggressive behaviors, or a combination thereof, in said subject as measured using the Personal and Social Performance (PSP) scale.

Yet another aspect of the invention provides a method of improving mental functioning and/or social integration in a human subject having schizophrenia, wherein said schizophrenia has been previously stabilized by administration of oral risperidone, the method comprising administering to the subject a long-acting injectable (LAI) depot composition comprising a maintenance dose of risperidone, wherein said composition is administered intramuscularly once about every 28 days or about once monthly, thereby improving mental functioning and/or social integration in said subject as measured using the patient-reported 20-items scale Subjective Well-Being Under Neuroleptics Treatment (SWN-20); and/or improving personal or social relationships, social useful activities, or reducing disturbing and aggressive behaviors, or a combination thereof, in said subject as measured using the Personal and Social Performance (PSP) scale.

In some embodiments, for the depot composition, the mass ratio of risperidone to (PLGA+risperidone), expressed as the percentage of the drug weight with respect to total weight of the drug plus polymer, is in the range of about 30-35% wt, about 31-35% wt, about 32-34% wt, or about 33% wt.

In some embodiments, the concentration of the PLGA in the depot composition is in the range of 24%-50% wt, 24%-40% wt, about 24%-30% wt, about 25-27% wt, or about 26% wt, (expressed as the percentage of polymer weight based on total composition weight).

The composition used in the method of the invention may be provided as a pharmaceutical kit that forms said composition. In some embodiments, the drug and the biocompatible polymer are contained in a first container, and the DMSO is contained in a second, separate container. Preferably, at least one of the first and second containers is a syringe, a vial, a device or a cartridge, either disposable or not and more preferably both the first and the second containers are disposable syringes. The containers can be syringes, vials, carpules, ampoules, devices or cartridges. In another embodiment, each of the three ingredients is contained in its own container. In another embodiment, the DMSO and risperidone are contained in a first container and the polymer is contained in a second container. When required, the contents of containers can be combined, for example through a connector or by using male-female syringes, and mixed each other so that the compositions according to the invention are reconstituted, for example by moving forwards and backwards the plungers of the syringes.

Accordingly, the method of treatment can further comprise the step(s) of a) providing a pharmaceutical kit comprising at least two containers within which the ingredients of the LAI depot composition are divided, and mixing the contents of said containers to form said composition; b) providing a pharmaceutical kit comprising at least two containers within which the ingredients of the LAI depot composition are divided and mixing the contents of a first container with the contents of a second container to form said composition, wherein said first container comprises PLGA and risperidone and said second container comprises DMSO; c) providing a pharmaceutical kit comprising at least two containers within which the ingredients of the LAI depot composition are divided and mixing the contents of a first container with the contents of a second container to form said composition, wherein said first container comprises risperidone and said second container comprises PLGA and DMSO; or d) providing a pharmaceutical kit comprising plural containers within which the ingredients of the LAI depot composition are divided and mixing the contents of said plural containers to form said composition, wherein said plural containers comprise a first container comprising risperidone, another container comprising PLGA, and another container comprising DMSO. In some embodiments, the kit comprises a single dose of risperidone.

The invention includes all combinations of the aspects, embodiments and sub-embodiments set forth herein.

8.42). The error bars represent SE and P values are for 75 mg dose and 100 mg dose group versus placebo (*p<0.01, p<0.001, *p<0.0001).

Figure 1:
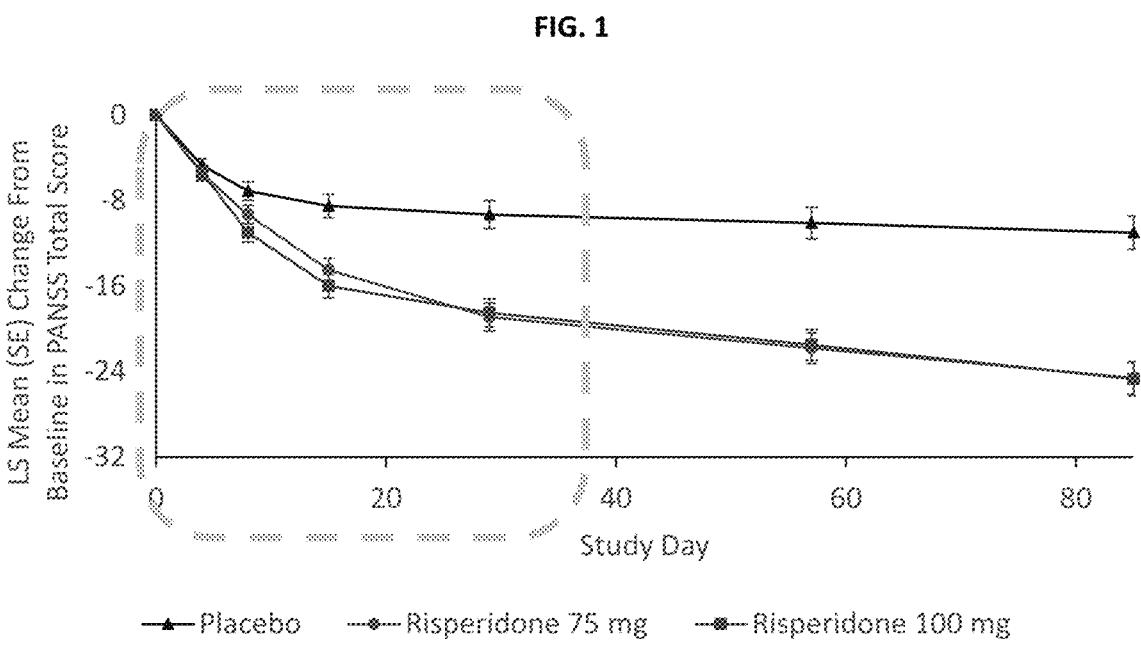
FIG. 1 depicts a graph of the mean change from baseline in total PANSS score versus days during the course of three administrations of the LAI depot composition of the invention (75 mg dosage strength, 100 mg dosage strength, placebo). LS mean change from baseline at each time point (mITT population) for PANSS total score, where mean PANSS score at baseline for placebo=96.4 (SD: 7.21), for 75 mg dose=96.3 (SD: 8.47) and for 100 mg dose=96.1 (SD.
Figure 2:
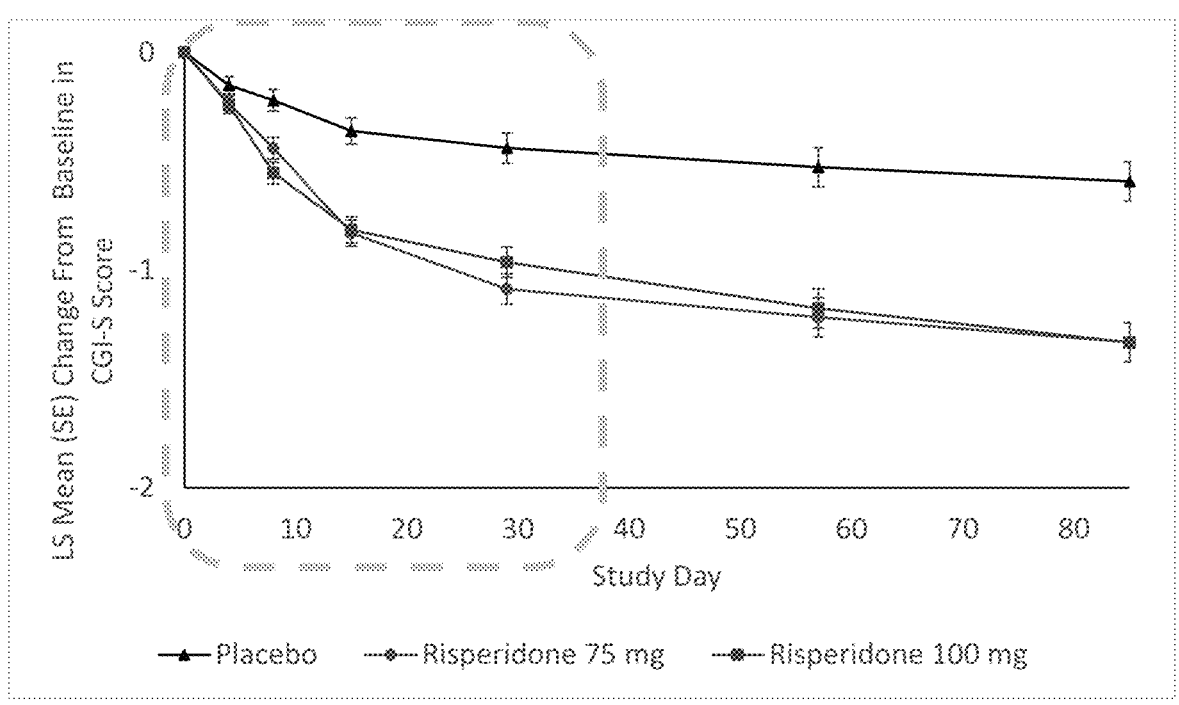

FIG. 2 depicts a graph of the mean change from baseline in CGI-S score versus days during the course of three administrations of the LAI depot composition of the invention (75 mg dosage strength, 100 mg dosage strength, placebo). LS mean change from baseline at each time point (mITT population) for CGI-S Score, where mean CGI-S score at baseline for placebo=4.9 (SD: 0.54), for 75 mg dose=4.9 (SD: 0.63) and for 100 mg dose=4.8 (SD: 0.53). The error bars represent SE and P values are for 75 mg dose and 100 mg dose group versus placebo (*p<0.01, **p<0.0001).

Figure 3:
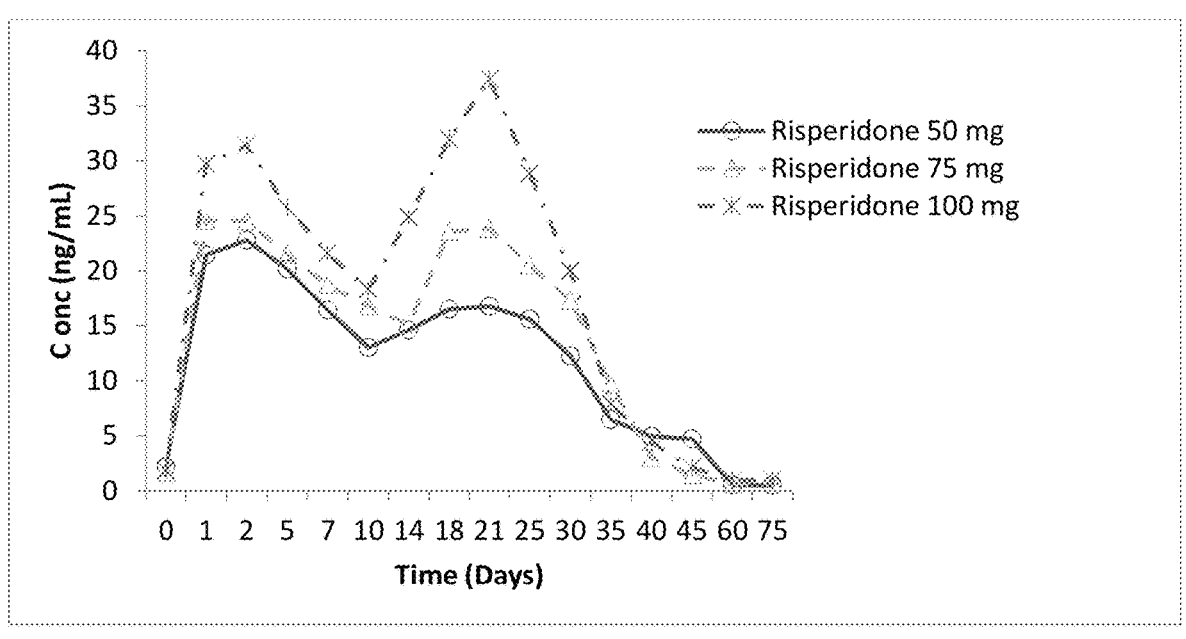

FIG. 3 depicts the mean plasma concentration profile for the total active moieties (risperidone plus 9-OH-risperidone) following intramuscular administration of three dosage strengths (50 mg, 75 mg, and 100 mg of risperidone) of a LAI depot composition.

Figure 4A:
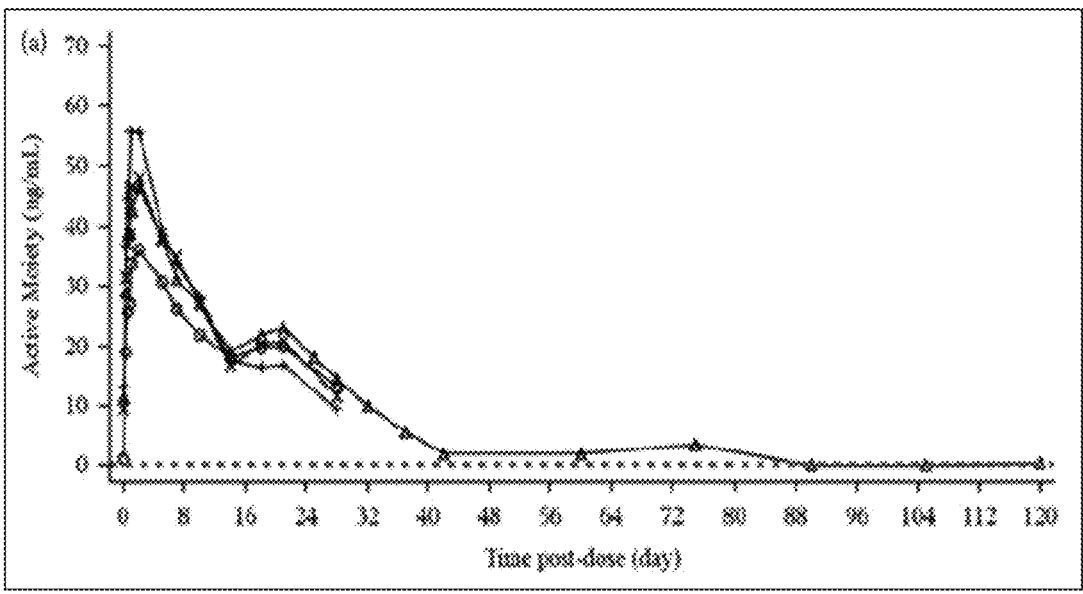
Figure 4B:
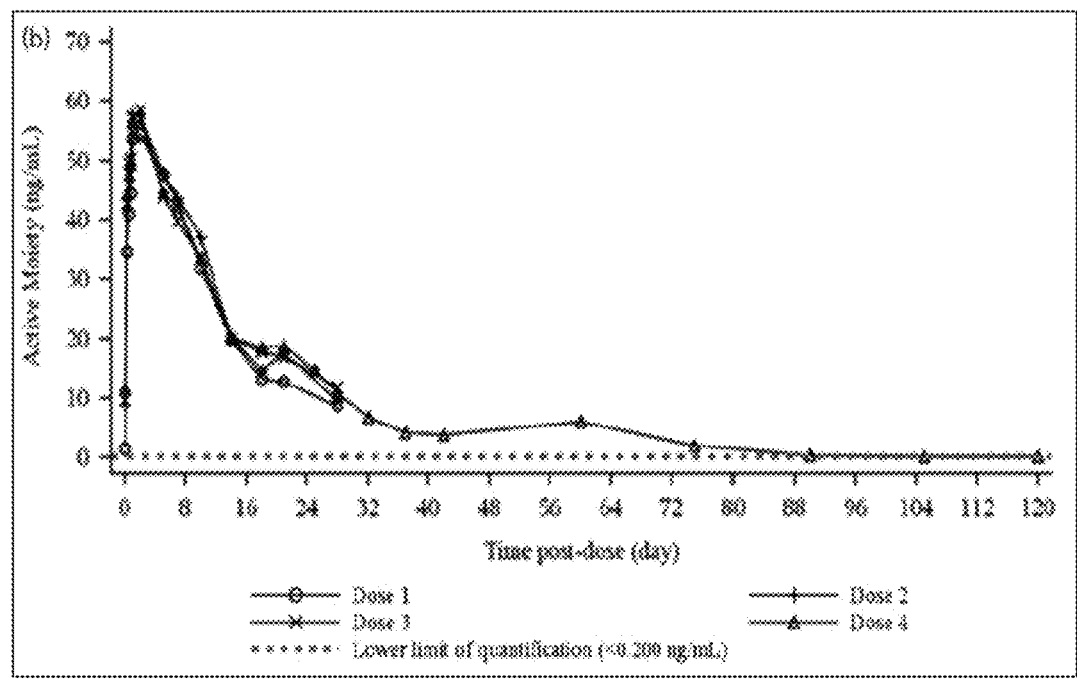

FIGS. 4A and 4B depict the mean plasma concentration profile for the total active moieties (risperidone plus 9-OH-risperidone) following repeated (four total administrations) once-every 28 days intramuscular administration of 75 mg of risperidone in a LAI depot composition to the gluteal muscles (FIG. 4A) and deltoid muscles (FIG. 4B).

Figure 5A:
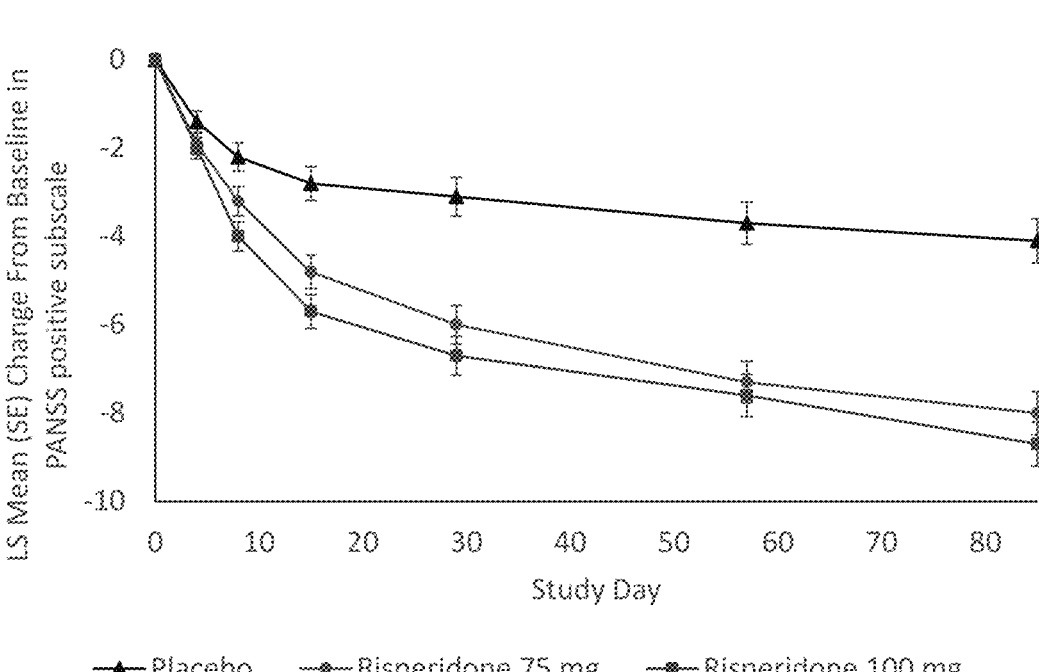
Figure 5B:
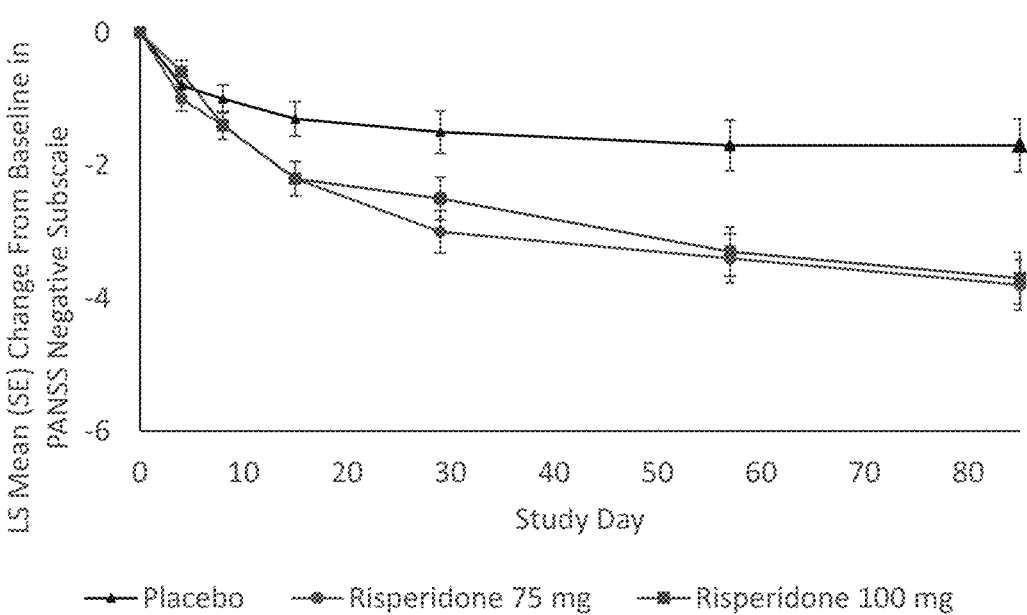
Figure 5C:
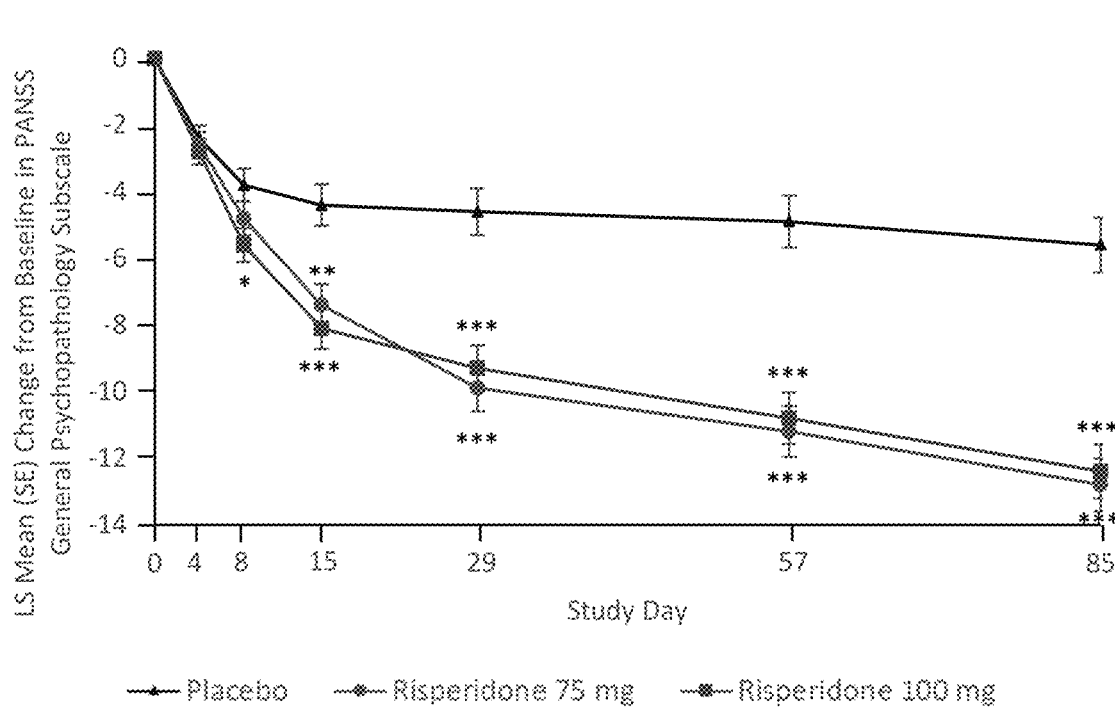

FIGS. 5A-5C depict graphs of the mean change from baseline in PANSS score (FIG. 5A: positive subscale; FIG. 5B: negative subscale; FIG. 5C: general psychopathology subscale) versus days during the course of three administrations of the LAI depot composition of the invention (75 mg dosage strength, 100 mg dosage strength, placebo). LS mean change from baseline in PANSS subscale score (mITT population): FIG. 5A-PANSS positive subscale, where mean PANSS positive subscale score at baseline for placebo=25.3 (SD: 3.11), for 75 mg dose=25.1 (SD: 3.15) and for 100 mg dose=25.5 (SD: 3.40). The error bars represent SE and P values are for 75 mg dose and 100 mg dose group versus placebo (*p<0.05, p<0.001, *p<0.0001); FIG. 5B-PANSS Negative Subscale, where mean PANSS score at baseline for placebo=23.5 (SD: 3.34), for 75 mg dose=23.3 (SD: 4.19) and for 100 mg dose=23.1 (SD: 3.73). The error bars represent SE and P values are for 75 mg dose and 100 mg dose group versus placebo (*p<0.05, p<0.01, *p<0.001); and FIG. 5C-PANSS General Psychopathology Subscale, where Mean PANSS Score at baseline: for placebo=47.7 (SD: 4.90), for 75 mg dose=47.8 (SD: 5.48) and for 100 mg dose=47.4 (SD: 5.06). The error bars represent SE and P values are for 75 mg dose and 100 mg dose group versus placebo (*p<0.05, p<0.001, * p<0.0001).

Figure 6:
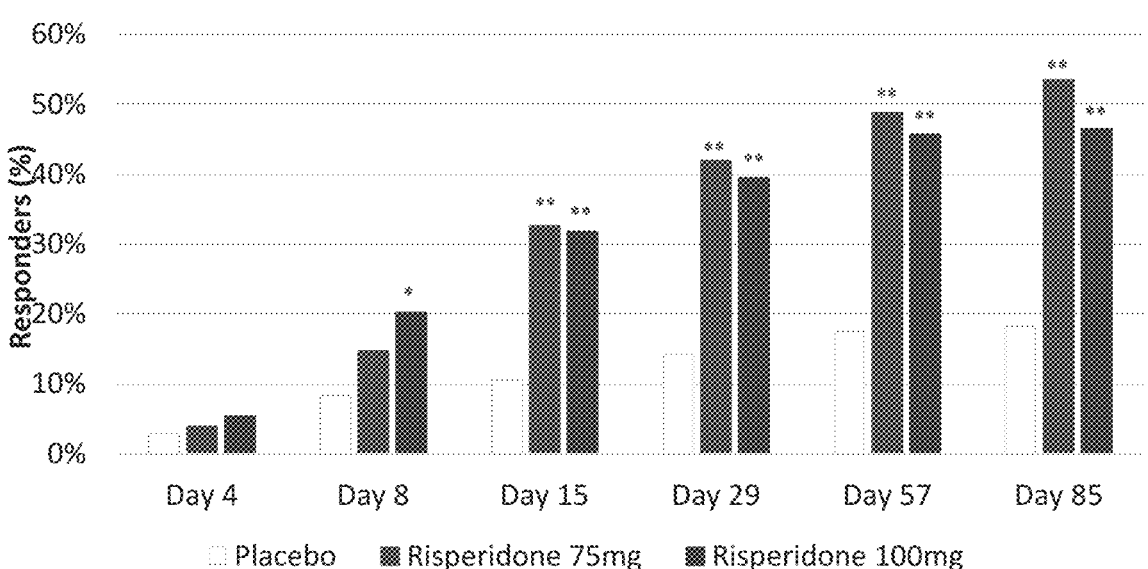
Figures 7A, 7B, 7C, 7D:
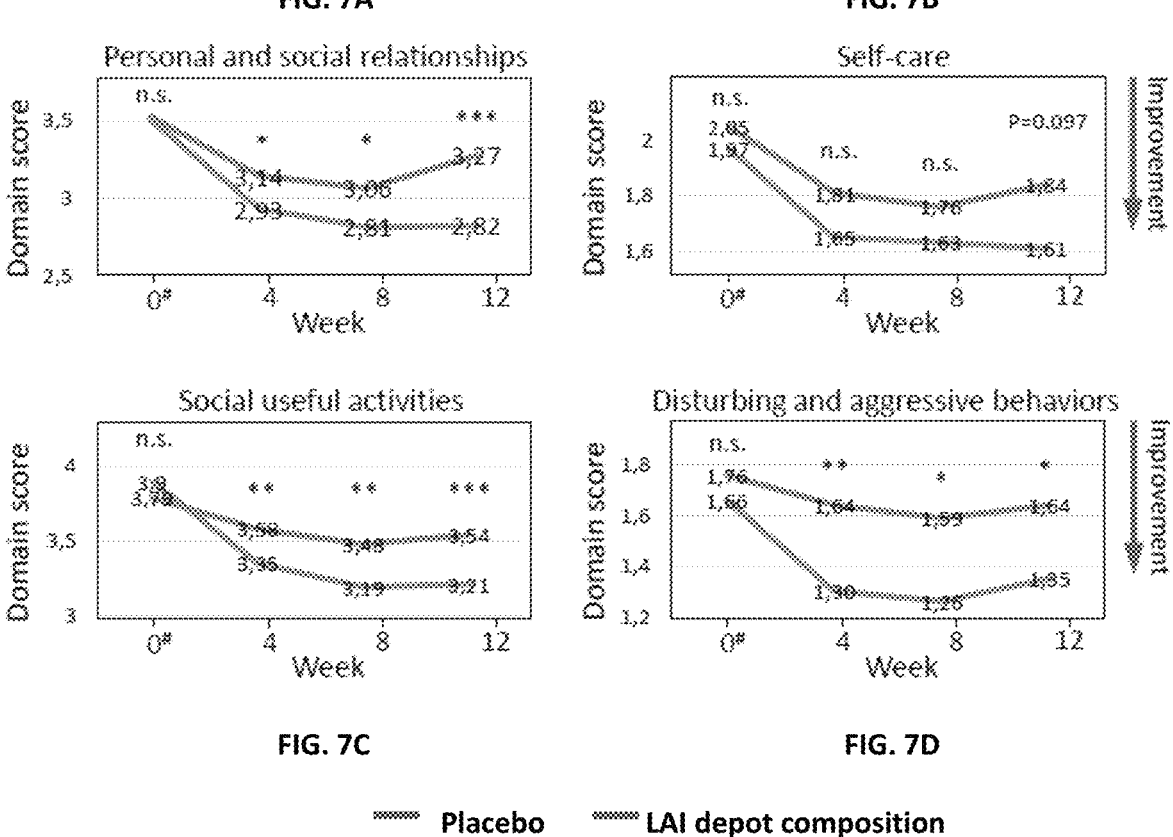

FIG. 6 depicts a chart of the overall response rate at the specified time points measured from the first day of administration during the course of three administrations of the LAI depot composition of the invention (75 mg dosage strength, 100 mg dosage strength, placebo). Overall response rate at each time point (mITT Population): Where the responders are those patients who achieved a decrease from baseline in PANSS Total Score >30% or CGI-I (Clinical Global Impression-Improvement) at least much improved. Dropouts prior to a presented time point are treated as non-responders and those patients who do not achieve a response are censored on the day of withdrawal/completion from the treatment. Presented statistics, frequencies, and denominator used for percentages are based on all patients in the ITT population and the randomized treatment. *p<0.01, **p<0.0001.

FIGS. 7A-7D depict graphs representing each of the 4 domain mean scores measured by the PSP scale. Smaller domain scores correspond to better functioning. A repeated measurement model was used for Placebo vs LAI depot composition group comparisons at each time-point. P-value is represented as: n.s., not statistically significant; *, p<0.05; , p<0.01; *, p<0.001. # denotes: Week 0 corresponds to baseline measurement.

DETAILED DESCRIPTION OF THE INVENTION

Unless otherwise specified, the term drug, metabolite and prodrug thereof are used interchangeably. In general, the term drug encompasses a metabolite and prodrug thereof.

As used herein, the term "loading dose" or "loading doses" refers to a) oral administration of a dose of risperidone to a subject on a daily basis for a period of plural days, wherein said loading doses are sufficient to establish in the subject a steady state plasma concentration of active moiety that is within a therapeutic range; and/or b) administration of one or more higher doses of LAI depot composition comprising risperidone prior to administration of a maintenance dose of LAI depot composition comprising risperidone, wherein said one or more higher doses are sufficient to establish in the subject a steady state plasma concentration of active moiety that is within a therapeutic range prior to administration of said maintenance dose.

As used herein, the term "maintenance dose" refers to an amount of LAI depot composition comprising a specified amount of risperidone, wherein said amount is administered to a subject from the first (initial) administration of said LAI depot composition through subsequent administrations (about once every 28 days or about once monthly) of said LAI depot composition. Said maintenance dose is sufficient to establish in the subject a steady state plasma concentration of active moiety that is within a therapeutic range without requiring administration of loading dose(s) of LAI depot composition comprising risperidone and without requiring oral supplementation with risperidone.

As used herein, the term "oral supplementation" refers to oral administration of a dose of risperidone to a subject on a daily basis after the subject has been administered a LAI depot composition of the invention.

As used herein and unless otherwise specified, the drug or active ingredient included in the injectable composition can be present in free base, salt, amorphous, crystalline, anhydrous, hydrate, optically pure, optically enriched or racemic forms thereof. Combinations of these various forms are also within the scope of the invention. A prodrug, metabolite (paliperidone) or derivative of the drug can also be included.

In some embodiments, the salt forms of risperidone can be made according to U.S. Publication No. 20040266791, the relevant disclosure of which is hereby incorporated by reference; however, other known salts can be used.

As used herein, the term "prodrug" is taken to mean a compound that is administered in an inactive (or less than fully active) form, and is subsequently converted to an active pharmacological agent through normal metabolic processes. A prodrug serves as a type of 'precursor' to the intended drug, e.g. risperidone, paliperidone or other drug.

As used herein, the term "derivative" is taken to mean a compound that is obtained by chemical modification of a parent compound such that the "derivative" includes within it almost all or all of the chemical structure of the parent (or base) compound. A derivative is a compound that is formed from a similar compound or a compound that can be imagined to arise from another compound, if one atom is replaced with another atom or group of atoms. A derivative is a compound derived or obtained from another and containing essential elements of the parent substance. A derivative is a chemical compound that may be produced from another compound of similar structure in one or more steps.

As used herein, the term "dosing period" refers to the period of days or weeks as measured from the initial day after administration of a dose to at least 28 days after administration or to administration of a subsequent dose. During the dosing period, the implant will provide therapeutic plasma levels of drug for about 4 weeks or more. A dosing period can end after expiration of a predetermined number of days or after the plasma level of drug drops below therapeutic levels.

As used herein, a "treatment period" refers to the weeks, months or years during which implants of the invention are administered to a subject. A treatment period generally comprises plural dosing periods. Dosing periods can occur sequentially or in an overlapping manner during a treatment period. For example, a first dose of injectable composition is administered and a second dose of injectable composition can be administered at a time following administration of the first dose, such that each dose will have its own corresponding dosing period, and the dosing periods would overlap. Dosing periods will typically be sequential or overlap by no more than one or seven days.

The intramuscular dose can be administered to any muscle or muscle group typically recognized by the pharmaceutical industry as a suitable site for an injectable composition. In some embodiments, the composition is administered to the gluteal and/or deltoid muscles. The composition can also be administered to the quadriceps muscle group. A dose can be administered to a single muscular site or can be divided into two or more portions and administered to two or more muscular sites of a subject. For example, a first portion of a dose can be administered to a first section of gluteal muscle and a second portion of the dose can be administered to a second section of gluteal muscle of a subject. The injectable composition can be administered to a subject in one or more injection sites on the same day and still be considered as being part of the same dosing period. For example, part of a dose can be administered to a first injection site and another part of the same dose can be administered to another injection site. A single-body implant will form at each injection site. Such a mode of administration within a same day is considered to be administration of a single dose with a single dosing period. Alternatively, administration can be modified such that there is one point of needle entry into the subject but more than one injection site below the skin, which can be achieved by making a first penetration into the skin and muscle and administering a portion of a dose, then partially withdrawing and redirecting the needle into another section of muscle, while maintaining the tip of the needle beneath the skin, and then injecting another portion of the dose into this other section of muscle. Such a mode of administration is still considered to be administration of a single dose within a single dosing period.

A therapeutically effective amount of injectable composition refers to an amount of injectable composition comprising a specified dose of drug. Accordingly, a therapeutically effective amount of 25-150 mg of injectable composition comprises a dose of 25-150 mg of risperidone; therefore, the actual amount of LAI depot composition administered would be greater than 25-150 mg, the actual amount of injectable composition being determined according to the content drug in the LAI depot composition. For example, a 75 mg dose of risperidone in a therapeutically effective amount of LAI depot composition comprising about 13 wt % of risperidone would be equivalent to therapeutically effective amount of about 577 mg, said composition comprising DMSO, risperidone, and PLGA. Similarly, a 100 mg dose of risperidone in a therapeutically effective amount of LAI depot composition comprising about 13 wt % of risperidone would be equivalent to therapeutically effective amount of about 769 mg, said composition comprising DMSO, risperidone, and PLGA.

Although not required, the present injectable composition can further comprise an alkaline agent. An alkaline agent with low water solubility such as lower than 0.02 mg/ml can be included. The alkaline agent can be present in a molar ratio >2/5 (drug/alkaline agent), meaning that the alkaline agent is present in molar excess over the drug. Preferred alkaline agents are alkaline or alkaline-earth hydroxides, such as magnesium hydroxide or aluminum hydroxide. Due to the limited water solubility of the alkaline agent, the d 0.5 of the particle size distribution, e.g. of the magnesium hydroxide, is preferably below 10 microns.

The method of the invention can employ a pharmaceutical kit suitable for in situ formation of a biodegradable solid implant in a subject in need thereof. In some embodiments, the kit comprises: a first container comprising risperidone; a second container comprising a biocompatible PLGA copolymer; and a third container comprising DMSO. By mixing the contents of the third container with the contents of the second container, a polymeric solution is formed, which solution is then mixed with the contents of the first container to form the injectable composition as described herein. In some embodiments, the copolymer and drug (and/or a metabolite and/or a prodrug thereof) are included in a first container, and DMSO is included in a second container. In some embodiments, the drug (and/or a metabolite and/or a prodrug thereof) is included in a first container, and PLGA and DMSO are included in a second container. In some embodiments, the containers are syringes and the mixing of their contents may be performed by direct or indirect connection followed by moving the plungers of the syringes forwards and backwards. Embodiments of the invention include those wherein a) drug and/or copolymer is present in solid form in a container prior to mixing with the solvent; or b) drug and/or copolymer is present in particulate form or as a lyophilizate in a container prior to mixing with the solvent (DMSO).

In some embodiments, the injectable depot composition is included in ready-to-use form in a single container stored at room temperature or under refrigerated condition. The ready-to-use form can be provided in a single-dose or multi-dose format.

The LAI depot composition can be prepared by mixing a polymeric solution with risperidone. As used herein, the term "polymeric solution" is taken to mean the fluid composition comprising a combination of DMSO and the polymer dissolved therein. In some embodiments, at least 80%, at least 90%, at least 95%, at least 99% or all of the polymer is dissolved in the DMSO. If not otherwise specified, the viscosity value of the polymeric solution or the injectable composition is given in Pa·s units.

If not otherwise specified, the viscosity value of the polymeric solution or the injectable composition is given in Pa·s units. The polymeric solution has a viscosity in the range of about 0.5 to about 3.0 Pa·s, about 0.7 to about 3.0 Pa·s, about 0.7 to about 2.0 Pa·s, about 1.5 to about 2.5 Pa·s, about 1.5 to about 2.3 Pa·s, about 1.5 to about 2.1 Pa·s, 1.5-2.1±10% Pa·s, 1.6-1.9±10% Pa·s, or 1.7-1.8±10% Pa·s. Before administration, the LAI depot composition has a viscosity in the range of about 1.0-7.0 Pa·s, about 1.5-7.0 Pa·s, or about 1.8-6.5 Pa·s. In some embodiments, the values may vary about ±10% from the specified limits. The viscosity can be controlled primarily according to the molecular weight (the intrinsic or inherent viscosity) of the polymer and the concentration of polymer in the injectable composition.

In some embodiments, the mass ratio of polymeric solution to drug, expressed as the mass of (polymer+solvent) to the mass drug, ranges from about 15:1 to about 5:1, about 12:1 to about 5:1, from about 7:1 to about 6.5:1, about 6.5:1 to about 6.8:1, about 6.67:1, about 6.66:1, or about 6.68:1.

In some embodiments, the mass ratio of polymer to polymeric solution, expressed as the weight percentage of polymer with respect to the weight of polymer+solvent, is about 25-50%, about 25-35%, about 30-40%, about 28-32%, or about 30%.

In some embodiments, the mass ratio of solvent (DMSO) to polymeric solution, expressed as the weight percentage of solvent with respect to the weight of polymer+solvent, is about 50-75%, about 65-75%, about 60-70%, about 68-72%, or about 70%.

The LAI depot compositions used in the method of the invention may comprise at least one polymer (or copolymer), DMSO, and risperidone. They may further comprise one or more pharmaceutical excipients suitable for intramuscular administration.

Following intramuscular administration, the LAI depot composition forms an in situ solid implant in the muscle tissue. When the implantable compositions are exposed to body fluids or water, the solvent (DMSO) diffuses away from the polymer-drug mixture and the polymer precipitates thereby trapping or encapsulating the drug within the polymeric matrix as the composition solidifies into a single implant at the injection site. The release of drug follows the general characteristics for diffusion or dissolution of a drug from within a polymeric matrix. Drug is also released by polymer erosion/degradation. The drug (active ingredient) forms a suspension or dispersion within a biodegradable and biocompatible polymeric solution to form an injectable composition that can be administered by way of a syringe (or pump) and a needle. In some embodiments, the implant begins release of risperidone within about 2 hours after administration to provide a rapid (e.g. less than 1 day, less than 18 hours, less than 12 hours, less than 6 hours, less than 3 hours) onset of action and continuously for at least 4 weeks. It provides therapeutically effective plasma levels of active moiety (risperidone+9-OH-risperidone) from the first day of administration for a period of at least 4 weeks.

The expression "about 50:50" as used in this description, refers to a monomer ratio of lactic to glycolic acid of biocompatible PLGA copolymer based on lactic and glycolic acid it is applied in the context of the invention for a monomer ratio measure with an standard technical error of ±10%. The commercially available grades of PLGA copolymer are known to vary slightly in their actual ratio of monomers even though they may be listed as having a 50:50 monomer ratio. For example, a copolymer specified as having a monomer ratio of 50:50 may actually have a monomer ratio ranging from 45:55 to 55:45 or 48:52 to 52:48. Accordingly, whenever the monomer ratio of "50:50" or "about 50:50" is specified herein, all ratios ranging from 45:55 to 55:45 are considered as being interchangeable therewith.

The compositions of the invention comprise a biodegradable poly(L-lactide-co-glycolide) copolymer (PLGA). The monomer ratio (L:G) of lactic acid to glycolic acid monomers present in the polymer can range from about 35:65 to about 75:25, about 50:50 to about 75:25, about 45:55 to about 70:30, about 50:50 to about 65:35, or about 65:35 to about 75:25, or said ratio can be 50:50±10% or 75:25±10%.

Inherent viscosity can be measured in chloroform at 25° C. or 30° C. at a concentration of 0.1% wt/v or 0.5% with a Ubbelhode size 0c or 0B glass capillary viscometer (RESOMER® grades) or in chloroform at 30° C. and at a concentration of 0.5% wt/v with a size 25 Cannon-Fenske glass capillary viscometer. Suitable grades of PLGA copolymers as described herein (according to molecular weight, intrinsic viscosity and/or molar ratio of lactic acid monomer to glycolic acid monomer) are end-capped (such as with an ester group, e.g. lauryl ester, methyl ester) are available from EVONIK® (Essen, Germany), Boehringer Ingelheim (Ingelheim am Rhein, Germany), ALKERMES (Dublin, Ireland) or SIGMA ALDRICH (ST. Louis, MO) and are marketed under the tradenames RESOMER®, LAKE-SHORE BIOMATERIALS™, or MEDISORB®. As the composition of some grades of end-capped PLGA is proprietary, the identity of the ester end-cap is not publicly available. Nonetheless, the performance properties of the grades of PLGA copolymer described herein are known and are used to characterize the material.

For the purpose of the present invention, throughout the present specification the term inherent viscosity ($\eta_{inh}$) of the polymer is defined as the ratio of the natural logarithm of the relative viscosity, $\eta_r$, to the mass concentration of the polymer, c, i.e.:

$$\eta_{inh}=(\ln\eta_r)/C$$

and the relative viscosity ($\eta_r$) is the ratio of the viscosity of the solution q to the viscosity of the solvent $\eta_s$, i.e.:

$$\eta_r=\eta/\eta_s$$

If not otherwise specified, the inherent viscosity and molecular weight values throughout the present specification are to be understood as measured with the method explained in example 1 (Method A and/or Method B). The value of inherent viscosity is considered in the present specification, as commonly accepted in the art, as an indirect indicator of the polymer molecular weight. In this way, a reduction in the inherent viscosity of a polymer, measured at a given concentration in a certain solvent, with same monomer composition and terminal end groups, is an indication of a reduction in the polymer molecular weight (IUPAC. Basic definitions of terms relating to polymers 1974. Pure Appl. Chem. 40, 477-491 (1974)).

The PLGA polymer in the LAI depot composition can have an inherent viscosity in the range of 0.20-0.60 dl/g, about 0.30-0.55 dl/g, about 0.36-0.52 dl/g, about 0.40-0.58 dl/g, or about 0.46-0.51 dl/g measured in chloroform at 30° C. and at a concentration of 0.5% wt with a Ubbelhode size 0B glass capillary viscometer.

The PLGA polymer in the LAI depot composition can have an average or mean molecular weight ranging from about 27-47 kDa, about 31-43 kDa, about 31-40 kDa, about 30-46 kDA, or about 30-36 kDa.

The PLGA polymer can be irradiated with a beta or gamma radiation at a dose of about 10 to about 30 kGy at a temperature between −40° C. and +35° C. Irradiation can serve to reduce the molecular weight of and/or to sterilize the PLGA polymer. In some embodiments, the polymer is radiated at a temperature lower than 35° C., more preferably lower than 25° C. and more preferably lower than 8° C. In a preferred embodiment of the invention, the biocompatible copolymer is gamma or beta irradiated in the dose range of 10-30 kGy±10% measured at a temperature between −40° C. to +35° C. to adjust its molecular weight to range from about 27-47 kDa, about 31-43 kDa, about 31-40 kDa, about 30-46 kDA, or about 30-36 kDa. In a more preferred embodiment, the polymer is radiated at 15-25 kGy±10% measured at the temperature of 8° C.

The concentration of the polymeric component in the compositions of the invention can be in the range of 20-50%, 24-50%, 24-34%, about 24-30%, about 25-27% or about 26% (expressed as the percentage of polymer weight based on total formulation weight). In some embodiments, at least 80%, at least 90%, at least 95%, at least 99% or all of the polymer is dissolved in the DMSO or injectable composition.

In some embodiments, the drug content ranges from about 4% to about 16% wt, about 7% to about 15% wt, about 10% to about 15% wt, about 12% to about 14% wt, or about 13% wt.

After administration, the injectable composition forms an implant that provides a satisfactorily controlled release profile for the drug. By "satisfactorily controlled" release profile is meant that the implant will exhibit an initial release profile that is not too steep (fast), which would otherwise lead to plasma levels that are too high with concomitant toxic side effects, and an initial release profile that is not too flat (slow), which would lead to plasma levels that are below therapeutic concentrations. An implant exhibiting a satisfactorily controlled initial release profile will release no more than 20% wt., no more than 15% wt, no more than 12% wt, no more than 10% wt, no more than 8% wt, no more than 6% wt, no more than 5% wt, no more than 4% wt, no more than 3% wt, no more than 2% wt or no more than 1% wt of its charge of drug within 24 hours after being placed in an aqueous environment. It will release at least 0.1% wt, at least 0.5% wt., at least 1% wt, at least 2% wt., at least 3% wt or at least 4% wt of its charge of drug within 24 hours after being placed in an aqueous environment. The invention includes all combinations of the embodiments herein.

The plasma concentration profile during the dosing period can exhibit one, two, or more maxima and one, two or more minima. An initial maximum can be caused by dissolution of drug during the initial day(s) of the dosing period followed by a slowing of the release thereof and another maximum can be caused by increased rate of release during the remaining days of the dosing period. Embodiments of the invention include those wherein: a) the plasma profile exhibits a maximum during the initial one to six days or one to three days of the dosing period; b) the plasma profile exhibits a maximum during the latter 10 to 24 days of a 4-week dosing period; c) the plasma profile exhibits a maximum during the initial days of the dosing period and a maximum during the remaining days of the dosing period; d) the plasma profile is substantially level (a standard deviation within ±30%, ±25%, ±20%, ±15%, ±10% or ±5% of the average or mean) during the dosing period; e) the plasma profile exhibits a maximum during the initial two to six days or two to twelve days of the dosing period; and/or f) the plasma profile exhibits a maximum during the latter 10 to 28 days of a 4- to 5-week dosing period.

In humans, the average plasma concentration of active moiety (risperidone+9-OH-risperidone) can range from about 3-200, about 5-80, or about 10-60 ng/ml when an amount of injectable composition equivalent to a dose of about 20-80 mg, about 37.5-125 mg, or about 50-100 mg of risperidone is administered. The average Cmin during the dosing period is in the range of about 1-80, 5-50, or about 5-40 ng/ml when an amount of injectable composition equivalent to a dose of about 25-150, about 37.5-125, or about 50-100 mg, respectively, of risperidone is administered. The average Cmax during the dosing period is in the range of about 8-300, 10-150, or 10-120 ng/ml when an amount of injectable composition equivalent to a dose of 25-150, 37.5-125, or 50-100 mg, respectively, of risperidone is administered. Some individual subjects may, on an equivalent dose basis, exhibit plasma concentrations outside the ranges specified herein for reasons such as poor health, advanced age, compromised metabolism, renal failure, disease, etc. Even so, a majority of subjects in a patient population to which the injectable implant is administered will exhibit plasma concentrations with those specified herein.

A more detailed clinical data analysis of pharmacokinetic performance of the LAI depot composition and method of the invention was conducted to determine a pharmacokinetic model for risperidone to correctly predict the active moiety profile in patients with schizophrenia. A population PK model was developed using active moiety concentrations from a study in healthy volunteers and two studies in patients with schizophrenia. Data from a comparative bioavailability study in medically stable patients and a Phase III trial in patients with acute exacerbation of schizophrenia were then incorporated, using empirical Bayesian feedback and model refinement in NONMEM. Also, covariate analysis was performed on CL40. The final model adequately described the pharmacokinetics of 6288 active moiety concentrations in 17 healthy volunteers and 430 patients with schizophrenia. This one-compartment disposition model had a complex absorption process, combining a small amount immediately entering the central compartment, two first-order absorption processes and a combined zero-order and first order process, with first-order elimination from the central compartment. Significant covariates on CL40 were BMI and sex. Goodness of fit plots and visual-predictive checks confirmed acceptable description of the data. Simulated profiles of active moiety concentrations following gluteal or deltoid injections of 75 mg or 100 mg administered 28 days apart showed that Risperidone LAI depot composition achieves a fast appearance of active moiety levels above therapeutic concentrations (10 ng/mL) and maintained sustained throughout the dosing interval. The table below provides the Median and 5th-95th percentiles for active moiety metrices simulated using the final population model for the first dose of risperidone LAI depot composition.

| Metric | 75 mg gluteal | 75 mg deltoid | 100 mg gluteal | 100 mg deltoid |
|---|---|---|---|---|
| Time to reach 10 ng/mL (h) | About 2 or 1-4 | About 1 or 1-24 | About 1 or 1-19 | About 1 or 1-13 |
| $C_{trough}$ (ng/mL) | About 20.9 or 7.79-45.7 | About 19.4 or 7.14-43.8 | About 27.9 or 10.4-61.0 | About 25.9 or 9.52-58.4 |
| $AUC_{tau}$ (ng*h/mL) | About 11931 or 6030-23060 | About 12302 or 6242-23651 | About 15908 or 8040-30746 | About 16403 or 8323-31535 |

The population PK model adequately described active moiety concentrations from five clinical studies after risperidone LAI depot composition administration. Relationships between active moiety exposure and covariates were defined to facilitate simulations for future studies. The model showed that risperidone rapidly achieves median therapeutic plasma levels of 10 ng/mL within 1-2 hours after the first injection and provides adequate active moiety concentrations throughout the dosing interval following once every four weeks injections.

The invention thus provides a method of treating an acute episode of schizophrenia administering to a subject a LAI depot composition comprising about 75 mg of risperidone in a polymeric solution of DMSO and PLGA copolymer, wherein said administering is intramuscular injection to deltoid or gluteal muscle tissue, whereby in said subject the time to reach a 10 ng/mL plasma concentration of active moiety is in the range of about 1-24 hours (average 1-2 hours), and the $C_{trough}$ is in the range of about 7-46 ng/mL (average 18-22 ng/mL).

The invention thus provides a method of treating an acute (moderate to severe) episode of schizophrenia administering to a subject a LAI depot composition comprising about 100 mg of risperidone in a polymeric solution of DMSO and PLGA copolymer, wherein said administering is intramuscular injection to deltoid or gluteal muscle tissue, whereby in said subject the time to reach a 10 ng/mL (h) plasma concentration of active moiety is in the range of about 1-20 hours (average 1 hours), and the $C_{trough}$ is in the range of about 9-62 ng/mL (average 25-29 ng/mL).

As used herein, whenever the plasma concentration of a drug is mentioned, such plasma concentration includes within it the sum total of the plasma concentration of the drug and its active metabolite(s). For example, whenever the plasma concentration of risperidone is mentioned, such plasma concentration includes within it the sum total of the plasma concentrations of risperidone and its active metabolite(s), such as 9-OH-risperidone (paliperidone).

In some embodiments, the particle size distribution of the drug is as follows: not more than 10% of the total volume of drug particles are less than 10 microns in size (equivalent diameter in volume as a function of applying Fraunhofer theory to irregularly shape particles; as measured by laser light scattering, such as with a Malvern Mastersizer 2000) and not more than 10% of the total volume of drug particles are greater than 225 microns (or 235 microns) in size. In addition, the drug particles possess a d0.5 value preferably in the range of about 60-130 microns. Accordingly, in some embodiments, the risperidone comprises a broad particle size distribution, which can be monomodal, bimodal or trimodal.

In some embodiments, the drug exhibits one of the following particle size distributions:

| Parameter | I | II | III | IV | V | VI |
|---|---|---|---|---|---|---|
| d0.1 (microns) | 27.49 | <30 | 17.41 | ≤20 | ≤10 | ≤10 |
| d0.5 (microns) | 79.90 | 40-130 | 51.61 | 40-130 | 40-130 | 40-130 |
| d0.9 (microns) | 176.66 | >170 | 175.32 | >170 | >225 or >235 | >200 |

In a preferred embodiment of the invention, this drug has the particle size distribution as follows:

not more than 10% of the total volume of particles is less than 10 microns in size;

not more than 10% of the total volume of particles is greater than 225 microns (or 235 microns) in size or not more than 10% of the total volume of particles is greater than 200 microns in size, and the d0.5 of the size distribution is in the range of about 60-130 microns, about 40-90 microns, or about 40-130 microns.

The particle size distribution was determined by light scattering technique using laser light diffraction in wet mode.

Embodiments of the invention include those wherein: a) the risperidone is present in solid form in the container prior to mixing with the solvent; b) the risperidone is present in particulate form or as a lyophilizate in the container prior to mixing with the solvent; c) the particle size distribution of the risperidone is as follows: not more than 10% of the total volume of drug particles are less than 10 microns in size and not more than 10% of the total volume of drug particles are greater than 225 microns (or 235 microns) in size; d) the d0.5 of the particle size distribution is in the range of about 60-130 microns; e) the mass ratio of the amount of polymeric solution (polymer+solvent) and to the amount of risperidone in the injectable composition ranges from about 15:1 to 5:1; f) the mass ratio of the amount of solvent and the amount of risperidone (mg solvent/mg risperidone) in the injectable composition ranges from about 12:1 to 4:1; g) the kit further comprises an alkaline agent; h) the mole ratio of risperidone to alkaline agent ranges from ⅔ to ⅖; i) the solvent, polymeric solution, risperidone and/or injectable composition is sterilized prior to administration; and/or j) the kit further comprises an alkaline agent in either or both containers.

Additional parameters such as the mass ratio of drug to polymeric solution (polymer+solvent), the mass ratio of drug to (polymer+drug), the mass ratio of solvent/drug, the mass ratio of polymer to polymeric solution (polymer+solvent), the mass ratio of solvent to polymeric solution (polymer+solvent), can also be useful to provide control over the initial release and/or controlled release of drug from the compositions of the invention.

In some embodiments, the drug is partially suspended in the composition and has a solubility in DMSO below about 10 mg/ml. In some embodiments, the drug is partially dissolved or substantially completely undissolved in the solvent, DMSO, polymeric solution or injectable composition. In some embodiments, ≤2.5%, ≤5%, ≤7.5%, ≤10%, ≤20% or <25%, of the drug is dissolved in the solvent or polymeric solution to form the injectable composition. In some embodiments, >0%, ≥0.5%, ≥1%, ≥5%, ≥10% or ≥15% or up to about 20% wt. of the drug is dissolved in the solvent or polymeric solution to form the injectable composition. All combinations of these embodiments are contemplated.

In yet another embodiment, the composition is a sterile composition. The composition may be sterilized by sterile filtration of the polymeric solution through a filtration medium having a nominal pore size of 0.22 microns or less, or by irradiation, or by a combination thereof.

The injectable composition can also be used to treat episodes of acute psychosis selected from the group consisting of delusional psychosis, psychotic depression, obsessive-compulsion disorder, schizophrenia, bipolar disorder, schizoaffective disorders, non-schizophrenic psychoses, Asperger's syndrome, Tourette's syndrome, obsessive-compulsion disorder, post-traumatic stress disorder, attention deficit hyperactivity disorder, personality disorders, aggression, depression, dementia, intellectual disabilities and behavioral disturbances in mental retardation and autism, autistic spectrum disorders, anxiety, eating disorders, nervous anxiety, insomnia, idiopathic dystonia, substance abuse, and any combination thereof. The injectable composition can also be used as an antihistaminic for the treatment of allergic disorders or as a prolactin secretion promoter for breastfeeding women or for the treatment of prolactin deficiency.

According to another aspect, the invention provides a pharmaceutical kit suitable for the in situ formation of a biodegradable implant in a body from the composition claimed, wherein the drug and the biocompatible polymer are contained in a first container, and the solvent is contained in a second, separate container. Preferably, at least one of the first and second containers is a syringe, a vial, a device or a cartridge, either disposable or not and more preferably both the first and the second containers are disposable syringes. This aspect of the invention is directed to a kit comprising a first container, preferably syringes, vials, devices or cartridges, all of them either being disposable or not, containing a polymer in solid form, such as PLGA and a drug in the appropriate amounts and a second container, likewise preferably syringes, vials, devices or cartridges, all of them being either disposable or not, containing the water-miscible solvent. When required, the contents of both containers are combined, for example through a connector or by using male-female syringes, and mixed each other so that the compositions according to the invention are reconstituted, for example by moving forwards and backwards the plungers of the syringes. Illustrative preferred embodiments are shown in FIG. 5 (syringes connected through a connector device) and in FIG. 6 (syringes connected through a direct thread).

According to another aspect, the invention provides a dosing regimen method for administering an injectable intramuscular depot composition according to the invention to a patient an episode of acute psychosis, the method comprising:
a) administering intramuscularly to the patient experiencing an episode of acute psychosis a first dose in the amount of 75 mg to 100 mg of risperidone on the LAI depot composition;
b) administering intramuscularly to said patient 75 mg to 100 mg of risperidone in the LAI depot composition, at a point of time on the 28$^{th}$ day, or on the 26$^{th}$ day to the 31$^{st}$ day counting from the previous administration day; and
c) repeating step b) whenever required.

Within a treatment period, administered doses of injectable composition are typically approximately the same.

According to an embodiment, the drug/(polymer+drug) mass ratio is about 33%, the content of drug is about 13% w/w of total formulation, and the viscosity of solution between polymer and DMSO is in the range of 1.5-2.5 Pa·s, more preferably in the range of 1.5-2.1 Pa·s and even more preferably in the range of 1.7-1.8 P·a·s.

According to another aspect the invention provides a dosing regimen method for intramuscularly administering an LAI depot composition according to the invention to a patient experiencing a first-time or recurrent episode of acute exacerbation of schizophrenia, the method comprising
a) administering intramuscularly to the patient experiencing an episode of acute psychosis a first dose in the amount of 75 mg to 100 mg of risperidone on the LAI depot composition;
b) administering intramuscularly to said patient 75 mg to 100 mg of risperidone in the LAI depot composition, at a point of time on the 28$^{th}$ day, or on the 26$^{th}$ day to the 31$^{st}$ day counting from the previous administration day; and
c) repeating step b) whenever required.

All values disclosed herein may have standard technical measure error (standard deviation) of ±10%.

Administration of a single dose is typically considered that amount of injectable composition administered to a subject within a period of up to 24 hours, up to 12 hours, up to 6 hours, up to 3 hours, up to one hour, up to 30 min, up to 15 min or up to 5 min.

A dose can be administered to a single muscular site or can be divided into two or more portions and administered to two or more muscular sites of a subject. For example, a first portion of a dose can be administered to a first section of gluteal muscle and a second portion of the dose can be administered to a second section of gluteal muscle of a subject.

As used herein, the term "dosing period" refers to the period of days or weeks as measured from the initial day after administration of a dose to at least 28 days after administration or to administration of a subsequent dose. During the dosing period, the implant will provide therapeutic plasma levels of drug for at least at least 4-5 weeks. A dosing period can end after expiration of a predetermined number of days or after the plasma level of drug drops below therapeutic levels.

As used herein, a "treatment period" refers to the weeks, months or years during which implants of the invention are administered to a subject. A treatment period generally comprises plural dosing periods. Dosing periods can occur sequentially or in an overlapping manner during a treatment period. For example, a first dose of injectable composition is administered and a second dose of injectable composition can be administered at a time following administration of the first dose, such that each dose will have its own corresponding dosing period, and the dosing periods would overlap. Dosing periods will typically be sequential or overlap by no more than one or seven days.

The injectable composition can be administered to a subject in one or more injection sites on the same day and still be considered as being part of the same dosing period. For example, part of a dose can be administered to a first injection site and another part of the same dose can be administered to another injection site. A single-body implant will form at each injection site. Such a mode of administration within a same day is considered to be administration of a single dose with a single dosing period.

Alternatively, administration can be modified such that there is one point of needle entry into the subject but more than one injection site below the skin, which can be achieved by making a first penetration into the skin and muscle and administering a portion of a dose, then partially withdrawing and redirecting the needle into another section of muscle, while maintaining the tip of the needle beneath the skin, and then injecting another portion of the dose into this other section of muscle. Such a mode of administration is still considered to be administration of a single dose within a single dosing period.

As used herein the term, "initial burst" or "initial release" refers to the addition of the plasma levels of drug plus those of active metabolite, which addition is also called "the active moiety" (risperidone and paliperidone together) throughout the present specification, from the moment of injection/administration of the injectable composition to a subject in need thereof until completion of the third day after the administration. For example, the drug can be risperidone and its metabolite can be paliperidone. In some embodiments, the initial period of release is within three days, within two days, within one day, within twelve hours, within 6 hours or within 2 hours after administration.

The method of invention was conducted according to Example 10 using the LAI depot compositions of Example 11. The following results were observed.

From 565 screened patients, 438 were randomized. One of them withdrew consent before receiving the study treatment; therefore 437 were included in the safety population, and 390 counted for the modified intent-to-treat (mITT) population. The study completion was highest in the risperidone 75 mg dose group (73.8%) and lowest in the placebo group (59.9%).

Demographic and baseline characteristics were similar among treatment groups. The patients had a mean age of 42 years; 67% were men, and 48.5% were white. Most subjects were enrolled in the USA (61.1%), and the mean BMI was 28.33 kg/m2. The mean (SD) PANSS score at baseline was 96.4 (7.21), 96.3 (8.47), and 96.1 (8.42) for placebo, 75 mg and 100 mg dose of risperidone, respectively.

There was a statistically significant difference of both risperidone groups versus placebo on PANSS total score mean change from baseline to Day 85. The placebo-adjusted Lawrence and Hung (LH) mean change from baseline to Day 85 was −13.0 (95% confidence interval (CI): −17.3 to −8.8; p<0.0001) and −13.3, (95% CI: −17.6 to −8.9; p<0.0001) for risperidone 75 mg and 100 mg, respectively (Hommel adjusted p value <0.0001, for both groups) (Table 2). In addition, the statistically significant improvement in PANSS total score mean change against placebo was shown as early as Day 8 for risperidone 100 mg (LS Mean difference, 95% CI: −3.9, −6.4 to −1.5; p=0.001), and Day 15 for risperidone 75 mg. These significant differences remained until the end of the study (Day 85).

For patients with baseline PANSS score 95, the placebo adjusted least square mean (LSM) difference in change from baseline to Day 85 was −13.8 (95% CI: −19.5 to −8.1) and −15.6 (95% CI: −21.4 to −9.9) for risperidone 75 mg and 100 mg group, respectively (p<0.0001 for both groups).

Significant differences versus placebo in mean change from baseline were observed at each assessment time point since Day 8 for PANSS Positive subscale, and Day 15 for PANSS Negative in both Risperidone groups, and since Day 8 for General Psychopathology subscales in risperidone 100 mg.

The placebo-adjusted CGI-S score LSM difference in change from baseline at endpoint was: −0.7 (95% CI: −1.0 to −0.5; p<0.0001) for 75 mg and −0.7 (95% CI: −1.0 to −0.5; p<0.0001), for 100 mg group (Hommel adjusted p value <0.0001, for both groups) (Table 2). LSM change from baseline at all assessments since Day 8 was significantly greater with both doses of risperidone compared with placebo.

For CGI-I score, the placebo-adjusted LSM difference at Day 85 was −0.8 (95% CI: −1.0 to −0.5) for risperidone 75 mg, and −0.7 (95% CI: −1.0 to −0.4) for risperidone 100 mg (p<0.0001 for both groups). These differences from placebo were significant at each assessment point from Day 8 and beyond for both risperidone doses.

For overall response rate at endpoint, the difference in proportions versus placebo was 39.2% (95% CI: 27.5-49.2) for risperidone 75 mg and 33.8% (95% CI: 22.0-43.8) for risperidone 100 mg (p<0.0001 for both groups, Mantel-Haenzel Test) (Table 2) translating into a number-needed-to-treat of three for both doses. The first significant difference from placebo in overall response rate was at day 8 for risperidone 100 mg (difference in proportion=11.8%; 95% CI: 3.3-20.5; p=0.005, Mantel-Haenzel test) and at Day 15 for risperidone 75 mg (difference in proportion=22.0%; 95% CI: 12.1-31.5; p<0.0001, Mante-Haenzel test). Similar results for the same efficacy outcomes were obtained when the full analysis set was evaluated.

Overall, 239 (54.7%) patients experienced at least one Treatment-Emergent Adverse Event (TEAE) (Supplementary Table 3), most of them were mild (67.8%) or moderate (28.0%). Of the TEAEs, 169 (38.7%) were considered related with the study treatment. The most frequently reported drug-related TEAEs in ≥2% of patients on placebo were dizziness and headache, whereas in both risperidone groups (75 and 100 mg) were blood prolactin increase, hyperprolactinaemia, akathisia, and headache.

No patient died during the study. Serious TEAEs were reported in 12 patients: 5 (3.4%), 2 (1.4%), and 5 (3.4%) with placebo, 75 mg and 100 mg of risperidone groups, respectively. Only one serious TEAE (agitation) was related to study drug in the risperidone 100 mg group. The incidence of patients who discontinued due to TEAE was 7.5% with placebo, 4.2% with Risperidone 75 mg and 6.2% in Risperidone 100 mg group.

Among treatment groups, the frequency of injection site reaction (ISR: redness, swelling, or induration) ranged from 6.1% with placebo, to 8.3% with risperidone 75 mg and 9.6% with risperidone 100 mg. Overall, the most frequently reported ISR was redness (6.2%), followed by swelling (1.8%). Patients reported median Visual Analog Scale (VAS) scores (0-10), indicating injection site pain were 2.0 in all study groups.

For hematology or biochemistry parameters, there were no notable differences between treatment arms from baseline through end of treatment and no notable changes in either treatment arm, except for prolactin. Prolactin values decreased in placebo group from baseline to end of treatment, whereas they increased in both risperidone groups, with mean (SD) endpoint prolactin levels being 220.6 (257.4) mIU/L with placebo, 875.4 (1080.7) mIU/L with risperidone 75 mg and 904.8 (810.6) mIU/L with risperidone 100 mg.

No noteworthy differences between treatment groups were documented for Columbia-Suicide Severity Rating Scale (C-SSRS). Two patients (1.4%) in each treatment group were documented to have had treatment-emergent suicidal behavior or ideation. Suicidal behavior or ideation worsened from baseline in two patients (1.4%) in the placebo group and one patient each (0.7%) in the risperidone 75 mg and 100 mg groups. No suicide attempts, aborted, or interrupted attempts were reported in any patient of any treatment group during the study.

The Abnormal Involuntary Movement Scale (AIMS), Barnes Akathisia Rating Scale (BARS), and Simpson-Angus Scale (SAS) were used to assess extrapyramidal symptoms. Regarding all three scales, treatment groups were comparable and no relevant changes from baseline to end of treatment were observed in any treatment group, i.e., mean scores (SD) for AIMS: 0.1 (1.36) for placebo, −0.1 (1.98) for risperidone 75 mg and −0.1 (1.22) for risperidone 100 mg; for BARS: 0.1 (0.98) for placebo, 0.0 (0.59) for risperidone 75 mg and 0.1 (0.87) for risperidone 100 mg, and for SAS: Mean (SD) 0.145 (2.5) for placebo, 0.085 (0.7) or risperidone 75 mg and 0.048 (1.2) for risperidone 100 mg.

Almost all patients (95.9%) took medication prior to the first dose of randomized treatment. The most common pharmacological groups of pre-baseline medications were antipsychotics (88.3%) and anxiolytics (27.5%). The most common medications were risperidone (59.3%), lorazepam (23.1%), quetiapine fumarate (16.9%), tropicamide (16.0%), and proxymetacaine hydrochloride (13.3%). Medications taken prior to the first dose of the randomized treatment were similar across treatment groups. No differences were noted in efficacy between patients who received different prior treatments.

Concomitant medications were taken by 56.5% of all patients during the study. The most common pharmacological groups were anxiolytics (37.8%), anti-inflammatory and antirheumatic products, non-steroidal anti-inflammatory agents (14.9%), and other analgesics and antipyretics (10.3%). The most common concomitant medications were lorazepam (34.6%), ibuprofen (13.7%), paracetamol (9.2%), and lisinopril (8.0%). There were no clinically relevant differences among the study groups.

The data obtained in the study demonstrate the efficacy, safety, and tolerability of risperidone-containing LAI depot composition and its method of use according to the invention in the monthly treatment of the acute schizophrenia. Superiority of active treatment versus placebo was shown for the primary efficacy outcome, with a statistically significant advantage of both risperidone 75 mg and 100 mg to placebo on PANSS total score mean change from baseline to Day 85 in the mITT population. The key secondary efficacy variable, CGI-S score mean change from baseline to Day 85, was also superior to placebo for both doses of risperidone.

Although comparisons between studies should be interpreted with caution because of the differences in patient characteristics and study methodology, the placebo-adjusted reduction of the PANSS total score with risperidone-containing LAI depot composition (−13.0 and −13.3) was higher than those obtained by other LAIs in similar acute schizophrenia studies, being approximately twice that of RBP-7000 90 mg/120 mg at 8 weeks (−6.1 and −7.2)13 and Paliperidone Palmitate 25 mg eq/100 mg eq/150 mg eq at 13 weeks (−5.1, −8.7, and −9.8), as well as similar to Aripiprazole once monthly 400 mg at 10 weeks (−15.1), 15 and Aripiprazole Lauroxil 441 mg/882 mg at 12 weeks (−10.9 and −11.9), 16 where patients received also oral aripiprazole during 2 and 3 weeks after randomization, respectively.

The onset of significant improvement in PANNS total and CGI-S score mean change was shown as early as Day 8 for the 100 mg dose and was maintained until the end of treatment period. Thus, the method of the invention addresses an unmet medical need and be used as an early antipsychotic therapy at the admission of acutely exacerbated schizophrenic patient for a rapid and effective reduction of severe or moderate psychotic symptoms.

Both risperidone groups were also superior to placebo for improving the patients' Positive and Negative Symptom Scores (PANSS), overall response rates, and CGI-I scores. Improvement in CGI-I scores and PANSS-positive symptom scores compared with placebo was shown as early as Day 8 and continued until Day 85.

Similarly, a significant improvement in overall response rate was also seen as early as Day 8 for risperidone mg and for risperidone 75 mg at Day 15, being significantly higher in both doses versus placebo, at all subsequent time points, with a high and clinically very meaningful number needed-treat of three.

Likewise, consistent results were demonstrated in the PANSS positive, negative, and General Psychopathology subscales. For the PANSS positive and negative subscales, statistical differences in mean change were obtained as early as Day 8 and Day 15 in positive and in negative subscales, respectively, demonstrating that the method may rapidly resolve not only positive symptoms but also negative symptoms, unlike another monthly injectable risperidone, in which changes in PANSS-negative scale scores was not significant different across the treatment and placebo groups.

In addition, the effect shown in the more severely ill subpopulation (≥95 PANSS total score at baseline) further demonstrate the robust efficacy of the method, and particularly with the dose of 100 mg, which produced at endpoint a particularly large reduction over placebo of 15.6 points in PANSS total score. This finding provides further evidence for the potential value of the method for the treatment of the acutely exacerbated schizophrenic patient who may need to be hospitalized owing to the severity of their symptoms.

Both doses of risperidone were well tolerated. The adverse events (AEs) observed were those expected for oral and LAI risperidone at therapeutic doses and were consistent with that observed in previous studies. All TEAEs were mainly mild or moderate in most patients in both treatment groups. Although the frequency of TEAEs was lower with placebo than in the risperidone groups, the rate was similar to those reported in a similar study in acute schizophrenia, and slightly lower to those observed in previous LAI risperidone study. Furthermore, both risperidone groups were associated with lower rate of discontinuation owing to TEAE compared with placebo, and no patient died owing to a TEAE during the study.

Generally, the incidence of serious TEAEs and of TEAEs, leading to study drug discontinuation was low and no clear differences between treatment groups were observed. Similarly, the frequency of ISRs (redness, swelling, or induration) was low overall, with redness being the most frequent in all treatment groups, and with a slight trend for a dose-dependent increase of ISRs. No relevant differences between treatment groups were seen in the 0-10 Visual Analog Scale (VAS) score, with a median value of 2.0 in all treatment groups, which is a clinically meaningful result for a new LAI formulation. Similarly, the EPS, akathisia, dyskinesia, and suicidality safety scales also did not indicate significant differences between either dose of risperidone and placebo. There were further no significant differences in laboratory measures between treatment arms from baseline through end of the study and no notable changes in either treatment arm, except for prolactin. The events related with the prolactin increase were between the more frequently reported TEAEs in this study, with a comparable incidence to that described by others. Several limitations need to be considered when interpreting the study results.

The data shown here indicate that the method of the invention in combination with the LAI depot composition as defined herein could be a clinical option both for the acute and maintenance treatment of schizophrenia. Patients with schizophrenia suffering a relapse need urgent attention owing to the severity of the symptomatology and future consequences if not treated immediately. The combination of the method and compositions provide a new monthly LAI antipsychotic that provides immediate and sustained drug plasma levels without plural loading doses of risperidone in said LAI depot composition and without oral supplementation with risperidone. Risperidone doses of 75 mg or 100 mg in the LAI depot composition were well tolerated and provided significant improvement of the symptomatology and disease severity in acutely exacerbated patients with schizophrenia. Moreover, this efficacy was observed as early as at the 8th day after first injection and was further improved up to 12 weeks, without requiring any loading doses of LAI depot composition and without requiring supplementation with oral risperidone.

Thus, method of the invention can be an effective therapeutic strategy at the admission of patients with schizophrenia suffering from an acute episode with severe or moderate psychotic symptoms.

A phase III multicenter, randomized, double-blind (DB), placebo controlled clinical trial and an open-label extension (OLE) clinical trial were conducted according to Example 12 using the risperidone-containing LAI depot composition described herein. The baseline sociodemographic and clinical characteristics of patients were similar comparing DB and OLE phase. Patients from the DB phase had a mean age of 42 years, over two-thirds were male and black and white races were equally represented (49.4% vs 49%, respectively). In the OLE phase, patients were younger, with a mean age of 39.3 years, almost two-thirds were male (60.9%), with a strong prevalence of Caucasian (84.7%) compared to other races.

In the DB phase, the study groups were very similar in terms of PANSS total score at baseline (mean±SD 96.1±7.25 for placebo arm versus 96.1±8.43 for pooled LAI depot composition 75 mg and 100 mg risperidone arms). In the OLE phase, the following PANSS total scores (mean±SD) were collected at baseline: 60.27±8.25 for the stable patients group; 70.02±14.35 for the stabilized patients group, and 82.34±12.30 for the unstable patients group.

At baseline of the DB phase, mean PSP total score was 49.9 (95% CI=49-51) for the LAI depot composition group, and 50.5 (95% CI=49-52) for the placebo group. Throughout the DB phase, subjects in LAI depot composition group consistently received higher overall ratings for personal and social functioning. By Visit 14, subjects in LAI depot composition group showed a significantly improved total score if compared to baseline, and a significantly higher total score compared to subjects in placebo group (LAI depot composition: mean 60.6 [95% CI=59-62]; placebo: mean 54.5 [95% CI=53-56]). More specifically, at visit 14, the mean PSP total scores improved by 10.7 points for the LAI depot composition group compared to 4.7 points for the placebo group (p<0.0001). LAI depot composition group also showed significantly greater improvement (p<0.05) than placebo group in all domains of PSP, except for 'Self Care' based on clinicians' assessment. FIGS. 7A-7D depict graphs representing each of the 4 domain mean scores measured by the PSP scale. Smaller domain scores correspond to better functioning. A repeated measurement model was used for Placebo vs LAI depot composition group comparisons at each time-point. P-value is represented as: n.s., not statistically significant; *, p<0.05; , p<0.01; *, p<0.001.

In terms of domains measured by the PSP, at baseline of the DB phase, 47% and 57% of subjects from the LAI depot composition and placebo groups received a 'Marked' rating for the 'Personal and social relationship domain'. By visit 14, the proportions had decreased to 16% and 33%, respectively, with a larger absolute decrease in proportion observed in the LAI depot composition group. Considering the domain 'Socially useful activities including study and work', 78% of pooled LAI depot composition subjects and 70% of subjects in placebo group received at baseline evaluation of moderate to severe impairment ('Marked' and 'Severe'). At visit 14, these proportions decreased in both the LAI depot composition and placebo groups, with a greater reduction for subjects in the LAI depot composition arms compared to those in the placebo arm (45.3% vs 57.5%, respectively). Finally, for the 'Disturbing and aggressive behaviors' domain, the proportion of subjects with an 'Absent' rating had increased from 48% at baseline to 74% at the end of the 3-month DB phase for the LAI depot composition group, while only a small improvement was observed for the placebo group (47% at baseline to 50% at visit 14).

Over the course of the OLE phase (between visit 4 and visit 14 during the OLE phase), mean total score for PSP had minimally improved for all 3 groups with no notable intragroup changes in the distribution across ratings for each domain. The difference in mean total score between visits from visit 4 (Day 85) up to visit 14 (Day 365) were <2 points in all 3 subgroups. Throughout the 12-months follow-up phase, subjects from de novo group consistently maintained a mean total score above the other groups.

Compared to their baseline for DB phase, subjects in LAI depot composition and placebo groups had significantly improved their personal and social functioning in all domains and PSP total score (p<0.0001) at all follow-up time points in the OLE phase (visit at 12, 24 and 52 week). For subjects who rolled over from the DB phase, their first assessment of PSP during the OLE phase was Visit 4, while de novo subjects were administered baseline assessment. Therefore, for rollover subjects, their PSP total score at Visit 14 of the DB phase was used as their baseline of OLE phase to enable calculations of a change from baseline on assessment intervals aligning with the de novo subjects. For these rollover subjects, intragroup comparisons showed that all had significantly improved (p<0.0001) their PSP domain and total scores throughout the OLE phase with reference to their status at baseline of DB phase (FIG. YY). Patients in the stable group, previously treated with oral risperidone, showed stable disease at the time of entering the OLE segment and maintained a stable PSP total score in all the follow-up timepoints, with minimal variations on the mean PSP total score and each domain (vs baseline: week 12, +1.22; week 24, −0.09; week 52, +1.11, respectively).

The health-related quality of life (HRQoL) was determined using the SWN-20 scale at the same timepoints that the PSP scale used. At baseline of the DB phase, mean SWN-20 score was comparable between LAI depot composition and placebo groups. Both LAI depot composition and placebo groups increased their mean values compared to their baseline; however, when comparing between groups, there is a trend of an increase of mean SWN-20 total score in the LAI depot composition vs placebo, especially at weeks 4 and 12, although it did not reach statistical significance, while can be observed a statistical significance in two subscales: Mental Functioning (p=0.0184) and Social Integration (p=0.0357).

Regarding the OLE phase, SWN-20 total scores in the different groups were similar to those in the PSP total scores, previously described. Thus, unstable patients showed a clear improvement in HRQoL compared to baseline, with statistically significant differences at all timepoints; stabilized patients showed a lesser extent improvement, with statistically significant results at week 52; while stable patients maintained consistent SWN-20 total scores. It is important to note that subjects in LAI depot composition group reported significantly greater improvement in 'Mental functioning' (p=0.0347) and 'Social integration' (p=0.0391) domains by visit 14 (ITT population), similarly to what was observed in the DB phase analysis.

In this randomized, double-blind, placebo-controlled trial, schizophrenia patients who were treated with LAI depot composition, experienced a significant improvement in their level of functioning over time and showed a similar trend regarding quality of life.

Over the DB and OLE phases, subjects showed an improvement in personal and social performance and well-being perception. The functional improvement was found significantly greater for the LAI depot composition group compared to placebo group in the DB phase, starting as soon as 4 weeks after starting the treatment.

The differences were statistically significant starting from week 4, and with the largest difference at the end of the study period, week 12. Importantly, 3 of the 4 subscales included in the PSP showed significant improvements with LAI depot composition as early as 4 weeks and these were maintained throughout the study: personal and social relationships, social useful activities, and disturbing and aggressive behaviours. These 3 domains are key components of the functioning of patients with schizophrenia.

Regarding the health-related quality of life, SWN-20 total scores were increased in both placebo and LAI depot composition groups, with a trend of not statistically significant higher scores in the LAI depot composition group. On the other hand, it should be emphasized that the improvement was statistically significant in two relevant subscales of NSW-20: mental functioning and social integration. In particular, the latter seems to be clinically meaningful, since it can be considered as an indicator of improved ability to establish social relationships.

The 52-weeks OLE phase also provided the opportunity to further demonstrate long-term efficacy of LAI depot composition on personal and social functioning and perception of well-being (HRQoL). Long-term benefits of LAI depot composition were observed in the OLE phase, with positive performance scores not only in the unstable patients, but also in the stabilized ones who were continuing their treatment with LAI depot composition. Furthermore, LAI depot composition administration has proven to be a reliable alternative to oral risperidone, as seen in stable subjects in which functional outcomes were maintained during the OLE phase.

Significant intra-group improvements in PSP and SWN-20 scores were observed in rollover subjects from the DB phase, both unstable and stabilized patients. Unstable patients showed an improvement in both PSP (total score and individual domains) and SWN-20 scores, at all timepoints of the OLE phase. Similarly, stabilized patients improved total PSP scores through the course of OLE phase, with concomitant increasing of SWN-20 total scores at week 52.

In addition, stable patients included in the OLE phase allowed us to study the impact of LAI depot composition on schizophrenia in patients clinically stabilized with oral risperidone at the time of entering the study. These patients were less severely ill when entering the OLE phase, and nonetheless they showed a better personal and social functioning and perception of well-being. The maintenance of the same level of functioning and perception of well-being throughout the 12-months OLE phase highlighted the value of monthly LAI depot composition administration as a simple and effective option in case of switching from oral risperidone.

To our knowledge, this is the first placebo-controlled study with antipsychotic LAIs in patients with acutely exacerbated schizophrenia that has shown an improvement on functioning PSP scores as early as 4 weeks after initiating treatment. Since it is difficult to appreciate a change in social functioning in a such short time frame, these findings corroborate the value of LAI depot composition not only regarding its fast efficacy but also as a treatment able to improve patient relevant outcomes as QoL and functioning in the long-term. Also, the findings from the OLE phase are of real interest since they demonstrated the benefits of LAI depot composition in maintenance phase among patients already stabilized with oral risperidone.

While in the recent past the primary focus was on reducing clinical symptoms (positive, negative, and disorganized behavior) and their direct consequences, including discharge from long-term care and on relapse prevention, now it is established that this focus clearly does not address the majority of the problems experienced by people with schizophrenia, and symptomatic reduction is now viewed as only one of several meaningful treatment goals. Now, it is more widely accepted that recovery is possible, even to the extent of full absence of all symptoms and disabilities and that optimal recovery should be a concrete goal to achieve for people with schizophrenia. The concept of recovery includes freedom from troubling psychotic symptoms and relapses, satisfaction with life and daily activities, and suitable functioning in everyday life.

It is interesting to note that the effects of the LAI depot composition were reached without a stabilization phase with oral risperidone supplemental treatment or a loading dose, contrary to what happened with paliperidone palmitate (Brown et al., "Evaluation of paliperidone palmitate long-acting injectable antipsychotic therapy as an early treatment option in patients with schizophrenia" in Early Interven. Psych. (2020), 14, 428-438) and occurred sooner than observed with Risperidone Microspheres (Kaplan et al., 2013, vide supra).

Accordingly, the invention provides a method of improving mental functioning and/or social integration in a human subject having schizophrenia, wherein said schizophrenia has been previously stabilized by administration of oral risperidone, the method comprising administering to the subject a long-acting injectable (LAI) depot composition comprising a maintenance dose of risperidone, wherein said composition is administered intramuscularly once about every 28 days or about once monthly, thereby improving mental functioning and/or social integration in said subject as measured using the patient-reported 20-items scale Subjective Well-Being Under Neuroleptics Treatment (SWN-20); and/or improving personal or social relationships, social useful activities, or reducing disturbing and aggressive behaviors, or a combination thereof, in said subject as measured using the Personal and Social Performance (PSP) scale.

The invention also provides a method of switching a subject from treatment with a risperidone oral dosing protocol to treatment with a risperidone injectable dosing protocol using the LAI depot composition disclosed herein. A multicenter, open-label, once-sequence, comparative bioavailability study was conducted. Once daily 4 mg oral EU risperidone for 7 days was followed by 4 intramuscular injections of risperidone (100 mg) LAI depot composition at 28-day intervals. Mean steady-state concentration versus time profiles for risperidone, 9-OH risperidone, and risperidone active moiety (RAM) were characterized. After first injection, mean (SD) RAM (risperidone+9-OH-risperidone) plasma concentrations at 2 hours achieved similar levels (31.43±14.012 ng/mL) to mean average concentration observed on oral treatment at steady-state (28.37±14.490 ng/mL). Steady-state concentrations were achieved following dose 1 of LAI depot composition and were maintained to the end of the dosing period. Fluctuation in plasma concentrations (Fluc) of RAM after LAI depot composition met bioequivalence criteria compared to oral risperidone. Steady-state minimum concentration ($C_{min\ ss}$) approached BE criteria and steady-state maximum concentration ($C_{max,ss}$), area under the curve during the dosing interval ($AUC_{tau}$) and average concentration ($C_{ave}$), were slightly higher for LAI depot composition compared to oral risperidone (based upon RAM). Patients receiving less than 4 mg of oral risperidone per day were also evaluated to determine the proper dose of risperidone LAI depot composition for transitioning dosing protocols. It was determined that subjects receiving <4 mg/day of oral risperidone should be administered about 75 mg risperidone in the LAI depot composition disclosed herein, and subjects receiving ≥4 mg/day of oral risperidone should be administered about 100 mg risperidone in the LAI depot composition disclosed herein.

The data demonstrate that the LAI depot composition allows for rapid achievement of plasma levels similar to those observed at steady-state after oral risperidone treatment; therefore, direct switching of dosing protocols after 24 hours from the last oral risperidone dose to the risperidone LAI depot composition treatment can be done in stable schizophrenia patients with no time lag, while maintaining steady-state levels of the active moiety throughout treatment and without oral supplementation or loading doses.

The term "about" is intended to mean±20%, ±15%, ±10%, ±5%, ±2.5% or ±1% relative to a specified value, i.e. "about" 20% means 20±2%, 20±1%, 20±0.5% or 20±0.25%.

EXAMPLES

The following examples illustrate the invention and should not be considered in a limitative sense thereof.

Also in the sense of this invention, without limitation and in connection with the examples, acceptable plasma levels of active moiety during the initial burst phase are below 75 ng/ml in Beagle dogs when the doses administered are 2.5 mg active moiety/kg body weight.

Example 1: Measurement of Inherent Viscosity

Method A:
Equipment
    GPC chromatograph with triple detector (laser diffraction, viscosimetry, refraction index)
        Viscotek® GPCmax VE 2001 GPC SOLVENT/SAMPLE MODULE
        Viscotek® TDA 305 TRIPLE DETECTOR ARRAY
Reagents
    Tetrahydrofuran (THF) grade GPC stabilized with butyl hydroxyl toluene (BHT) 250 ppm
    Polystyrene narrow standard (preferable about a molecular weight of 90 or 99 kDa)
Sample Preparation
    1-2 mg/ml Standard Sample
    10 mg/ml Test sample: 3 samples for each polymer to be tested
Pre-Conditioning
    Condition and stabilize column and detectors with mobile phase (THF) until reaching working flow rate of 1 ml/min and purge viscometer and refraction index detectors, checking at the end that all signals are stable and adequate.
Chromatographic Conditions:
    Column: 2 serial columns i-MBMMW-3078 (CLM1012, Viscotek)
    Delay column: medium delay (CLM9002, Viscotek)
    Column temperature 30° C.
    Flux rate 1 ml/min
    Injection volume: 100 μl
    Run time: 35 minutes
    Eluent: stabilized THF (pre-heated to 30° C. and under 100 rpm agitation)

System Verification
    Inject 100 μl of eluent and check there is no response in signals related with molecular weight determination
    Inject 100 μl of polystyrene narrow standard and check adequacy of the measurement. Repeat at least twice.
    Acceptance Criteria: ±5% of the nominal Molecular Weight and ±3% Intrinsic Viscosity declared by manufacturer standard certificate.
Calibration
    Not necessary if system verification complies and no previous chromatographic conditions are changed.
    In case it would be required to calibrate:
    Inject 100 μl of polystyrene standard at least twice.
    Use first sample's data for triple calibration by creating a new multidetectors—homopolymer's method.
    Introduce into the method all the data needed for internal calibration such standard values of MW, IV, do/dc, dA/dc and refractive index of the solvent.
    Calibrate the system as the equipment specify and save the new method.
    Check with the new method the adequacy of the measurement for the second injection of the standard.
Procedure
    Inject by triplicate 100 μl of the test sample
    Polymer molecular weight measured according to the technique specified resulted in 32.5 Kda. According to a similar technique, inherent viscosity of the polymer resulted in a value of 0.27 dl/g. It is important to mention that inherent viscosity values correspond to those obtained with the technique described, specially related to temperature conditions and eluent used. Any change in measurement conditions mean the obtention of different values as directly depend on them.
Method B:
Equipment
Automated Capillary Viscosimetry
    Rheotek®-RPV-2 Automatic polymer viscosimeter
Reagents
    Chloroform HPLC grade
    Acetone
Sample Preparation
    0.5 mg/ml Test sample filtered: 2 samples for each polymer to be tested.
Conditions
    The test is carried out at the temperature of 30.0±0.1° C.
Procedure
    Measure in first time the solvent and later the sample. Filtered chloroform (solvent) or sample: Using a glass syringe, filter solvent or sample through a 0.45 μm PTFE filter discarding the first ml.
    Inject 12 to 15 mL of solvent or sample. Do not overfill the viscometer tube. The solvent or sample should be between lines as shown. It is important to mention that inherent viscosity values correspond to those obtained with the technique described, specially related to temperature conditions, concentration and solvent used. Any change in measurement conditions mean the obtention of different values as directly depend on them.

Example 2: Depot Formulation with Resomer® 503 without Radiation

In the present example, the following formulation was prepared:

| | Ingredient | Amount (mg) |
|---|---|---|
| Female 2.25 ml syringe | Lactic-co-glycolic acid copolymer (N-capped) with 50% content of each of the two organic acid monomers and a molecular weight of 32 KDa. | 50 |
| | Risperidone | 25 |
| Male 2.25 ml syringe | Dimethyl sulfoxide | 117 |

Risperidone particle size was characterized by light scattering and provided the following distribution of particle size: d(0.1)=27.49 μm, d(0.5)=79.90 μm and d(0.9)=176.66 μm.

Example 3: Depot Formulation with Resomer® 504 Radiated to 16 Kgy

The present example shows how the polymer molecular weight can be controlled in order to have a sterile formulation with the desired in vivo release properties.

Filling solid polymer in syringes represents a real challenge in the manufacturing of injectable formulations. The polymer, manufactured as a non-sterile product, requires undergoing sterilization in order to achieve a formulation that can be injected into human beings. Probably the best way to solve this technical issue is to subject the polymer to sterilization by gamma or beta irradiation. Irradiation represents a challenging issue when used biodegradable polymers, as irradiation can disrupt the chains into fractions of smaller size. Control of the polymer molecular weight appears as again as the critical parameter to control the final characteristics of a product after a sterilization process.

However, chain size reduction by irradiation can be mathematically modelled or controlled in order to predict the final molecular weight of a polymer to be used as raw material having a molecular weight higher than desired. Therefore, once determined the fill weight of the polymer to be filled in a container (for example, the fill weight of the polymer in a syringe) and the bio-burden present in the polymer as raw material, the irradiation dose required to get the polymer sterile (as specified by ISO 11137) is selected for the required fill weight.

Then the mathematical model describing the loss of molecular weight for a certain polymer versus the irradiated dose can identify the initial molecular weight of the polymer to be used as raw material required obtaining, after the irradiation process, a polymer with the desired final molecular weight for the formulation.

As the availability of a polymer with a specific molecular weight can be somewhat limited, then we can alternatively select an available polymer with a molecular weight that is higher to what is required according to the irradiation dose identified, and then adjust the irradiation dose to a higher value in order to obtain a sterile polymer with the required molecular weight. In this example, a lactic-co-glycolic acid copolymer with 50% content of each of the two organic acid monomers and a molecular weight of 38 Kda was sterilized by beta irradiation at 16 Kgy under controlled temperature and moisture conditions. The resultant polymer was characterized for its molecular weight according to the method described in example 1. Molecular weight after irradiation process was 31 Kda.

| | Ingredient | Amount (mg) |
|---|---|---|
| Female 2.25 ml syringe | Lactic-co-glycolic acid copolymer (N-capped) with 50% content of each of the two organic acid monomers and a molecular weight of 38 Kda, beta-irradiated as a bulk with a 16 Kgy dose achieving a final molecular weight of 31 Kda. | 50 |
| | Risperidone | 25 |
| Male 2.25 ml syringe | Dimethyl sulfoxide | 117 |

Risperidone particle size was characterized by light scattering and provided the following distribution of particle size: d(0.1)=27.49 μm, d(0.5)=79.90 μm and d(0.9)=176.66 μm.

Inherent viscosity of the irradiated polymer, as calculated by the technique described in example 1 was 0.27 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

Example 4: Depot Formulation with Resomer® 504 Radiated to 25 Kgy

This is another example that shows how the polymer molecular weight can be controlled in order to have a sterile formulation with the desired in vivo release properties.

A lactic-co-glycolic acid copolymer with 50% content of each of the two organic acid monomers and a molecular weight of 50 Kda was sterilized by beta irradiation at 25 Kgy under controlled temperature and moisture conditions. The resultant polymer was characterized for its molecular weight according to the method described in example 1. Molecular weight after irradiation process was 35 Kda.

| | Ingredient | Amount (mg) |
|---|---|---|
| Female 2.25 ml syringe | Lactic-co-glycolic acid copolymer (N-capped) with 50% content of each of the two organic acid monomers and a molecular weight of 50 Kda, beta-irradiated as a bulk with a 25 Kgy dose achieving a final molecular weight of 35 Kda. | 50 |
| | Risperidone | 25 |
| Male 2.25 ml syringe | Dimethyl sulfoxide | 117 |

Risperidone particle size was characterized by light scattering and provided the following distribution of particle size: d(0.1)=27.49 μm, d(0.5)=79.90 μm and d(0.9)=176.66 μm.

Inherent viscosity of the irradiated polymer, as calculated by the technique described in example 1 was 0.28 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

Example 5: Depot Formulation with Lakeshore Biomaterials® 5050 DLG 5E Radiated to 25 Kgy This is another example that shows how the polymer molecular weight can be controlled in order to have a sterile formulation with the desired in vivo release properties.

A lactic-co-glycolic acid copolymer with 50% content of each of the two organic acid monomers and a molecular weight of 56 Kda was sterilized by beta irradiation at 25 Kgy under controlled temperature and moisture conditions. The resultant polymer was characterized for its molecular weight according to the method described in example 1. Molecular weight after irradiation process was 45 Kda.

|  | Ingredient | Amount (mg) |
|---|---|---|
| Female 2.25 ml syringe | Lactic-co-glycolic acid copolymer (N-capped) with 50% content of each of the two organic acid monomers and a molecular weight of 56 Kda, beta-irradiated as a bulk with a 25 Kgy dose achieving a final molecular weight of 45 Kda. | 50 |
|  | Risperidone | 25 |
| Male 2.25 ml syringe | Dimethyl sulfoxide | 117 |

Risperidone particle size was characterized by light scattering and provided the following distribution of particle size: d(0.1)=27.49 μm, d(0.5)=79.90 μm and d(0.9)=176.66 μm.

Inherent viscosity of the irradiated polymer, as calculated by the technique described in example 1 was 0.28 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

Example 6: Depot Formulation with Resomer® 504 Radiated to 25 Kgy

In this example, a lactic-co-glycolic acid copolymer with 50% content of each of the two organic acid monomers and a molecular weight of 38 Kda was sterilized by beta irradiation at 25 Kgy under controlled temperature and moisture conditions. The resultant polymer was characterized for its molecular weight according to the method described in example 1. Molecular weight after irradiation process was 28 Kda.

|  | Ingredient | Amount (mg) |
|---|---|---|
| Female 2.25 ml syringe | Lactic-co-glycolic acid copolymer (N-capped) with 50% content of each of the two organic acid monomers and a molecular weight of 38 Kda, beta-irradiated as a bulk with a 25 Kgy dose achieving a final molecular weight of 28 Kda. | 50 |
|  | Risperidone | 25 |
| Male 2.25 ml syringe | Dimethyl sulfoxide. | 117 |

Risperidone particle size was characterized by light scattering and provided the following distribution of particle size: d(0.1)=27.49 μm, d(0.5)=79.90 μm and d(0.9)=176.66 μm.

Inherent viscosity of the irradiated polymer, as calculated by the technique described in example 1 was 0.25 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

Example 7: Depot Formulation with Resomer® 503 Radiated to 15 Kgy

In this example, a lactic-co-glycolic acid copolymer with 50% content of each of the two organic acid monomers and a molecular weight of 32 Kda was sterilized by beta irradiation at 15 Kgy under controlled temperature and moisture conditions. The resultant polymer was characterized for its molecular weight according to the method described in example 1. Molecular weight after irradiation process was 28.3 Kda.

|  | Ingredient | Amount (mg) |
|---|---|---|
| Female 2.25 ml syringe | Lactic-co-glycolic acid copolymer (N-capped) with 50% content of each of the two organic acid monomers and a molecular weight of 32 Kda, beta-irradiated as a bulk with a 15 Kgy dose achieving a final molecular weight of 28.3 Kda. | 50 |
|  | Risperidone | 25 |
| Male 2.25 ml syringe | Dimethyl sulfoxide | 117 |

Risperidone particle size was characterized by light scattering and provided the following distribution of particle size: d(0.1)=27.49 μm, d(0.5)=79.90 μm and d(0.9)=176.66 μm.

Inherent viscosity of the irradiated polymer, as calculated by the technique described in example 1 was 0.25 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

Example 8: Depot Formulation with Resomer® 504 without Radiation

|  | Ingredient | Amount (mg) |
|---|---|---|
| In this example, a lactic-co-glycolic acid copolymer with 50% content of each of the two organic acid monomers and a molecular weight (according to method described in example 1) of 48 Kda was used. Female 2.25 ml syringe | Lactic-co-glycolic acid copolymer (N-capped) with 50% content of each of the two organic acid monomers and a molecular weight of 48 Kda. | 50 |
|  | Risperidone | 25 |
| Male 2.25 ml syringe | Dimethyl sulfoxide | 117 |

Risperidone particle size was characterized by light scattering and provided the following distribution of particle size: d(0.1)=27.49 µm, d(0.5)=79.90 µm and d(0.9)=176.66 µm.

Inherent viscosity of the irradiated polymer, as calculated by the technique described in example 1 was 0.33 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

Example 9: Depot Formulation with Resomer® 504 Radiated to 25 Kgy

The current example demonstrates the concept is also valid to achieve an intramuscularly injectable risperidone formulation suitable to be administered once each 4 weeks.

A lactic-co-glycolic acid copolymer with 50% content of each of the two organic acid monomers and a molecular weight of 50 Kda was sterilized by beta irradiation at 25 Kgy under controlled temperature and moisture conditions. The resultant polymer was characterized for its molecular weight according to the method described in example 1. Molecular weight after irradiation process was 35 Kda.

| | Ingredient | Amount (mg) |
|---|---|---|
| Female 2.25 ml syringe | Lactic-co-glycolic acid copolymer (N-capped) with 50% content of each of the two organic acid monomers and a molecular weight of 50 Kda, beta-irradiated as a bulk with a 25 Kgy dose achieving a final molecular weight of 35 Kda. | 50 |
| | Risperidone | 25 |
| | Dimethyl sulfoxide | 117 |

Risperidone particle size was characterized by light scattering and provided the following distribution of particle size: d(0.1)=17.41 µm, d(0.5)=51.61 µm and d(0.9)=175.32 µm.

Inherent viscosity of the irradiated polymer, as calculated by the technique described in example 1 was 0.28 dl/g.

The risperidone implantable formulation was prepared by connecting male and female syringes and moving the plungers forwards and backwards upon complete dissolution of the polymer and the formation of a homogeneous suspension of the risperidone in the polymer dissolution.

Example 10: Clinical Evaluation of LAI Depot Composition

Study Design

This was a phase III multicenter, randomized, double-blind, placebo controlled clinical trial, which was conducted in the United States and Ukraine, in accordance with the Declaration of Helsinki, and Good Clinical Practice principles outlined in the International Conference on Harmonization. The protocol, amendments, and informed consent were approved by the Ethics Committee for each site, and written informed consent was obtained from all subjects before study participation.

The study consisted of a screening period of up to 8 days, immediately preceding the baseline day, followed by a treatment period of 12 weeks, which ended with a 2-week follow-up period. Eligible patients were randomly assigned 1:1:1 to double-blind intramuscular treatment with 75 mg or 100 mg of risperidone, in the risperidone LAI depot composition, or placebo. After initial dosing at baseline, each study drug was administered intramuscularly once every 4 weeks during the 12-week treatment period.

Patient Selection

Eligible subjects were 18-65 years old, with a current diagnosis of schizophrenia, according to the diagnostic and Statistical Manual of Mental Disorders, Fifth Edition criteria and a body mass index between 18.5 and 40.0 kg/m2. Patients were currently experiencing an acute exacerbation or relapse with a total score between 80 and 120 on the PANSS, 23 and a score ≥4 points for ≥2 of the following positive symptom items: delusions, conceptual disorganization, hallucinatory behavior, and suspiciousness/persecution. All patients had to score of (moderately ill or worse) on the Clinical Global Impression-Severity scale (CGI-S)24 and had previously had a clinically significant beneficial response after treatment with an antipsychotic other than clozapine.

Patients were excluded if improvement in PANSS total score was ≥20% between the screening visit and baseline, or with active suicidality, indicated by having answered "yes" on item 4 or 5 of the C-SSRS25 in the most recent episode (within the past 2 months) or having answered "yes" to any of the five items (suicidal behavior) with an episode occurring within the last year. Patients were also excluded for the presence of clinically significant comorbid neuropsychiatric disorder, lifetime history of schizoaffective or bipolar disorders, or a history of any unstable medical condition or laboratory abnormality that could interfere with the conduct of the study or compromise the well-being of the patient. Women who were pregnant or breastfeeding were also excluded.

Treatment Protocol

Risperidone, in the risperidone LAI depot composition (Laboratorios Farmaceuticos ROVI, S.A., Madrid, Spain) was available in a kit of two syringes, one containing risperidone plus poly lactic-co-glycolic acid (PLGA) in the form of a solid powder, and the other containing dimethyl sulfoxide, the solvent required for reconstitution. They were prepared according to Example 11. Matching placebo was also available in a 2-syringes kit, with a similar appearance but containing only PLGA in the solid power syringe. Eligible patients were randomized 1:1:1 in a double-blind fashion to risperidone, in the risperidone LAI depot composition, 75 mg, risperidone, in the risperidone LAI depot composition, 100 mg or placebo, injected into the gluteal or deltoid muscle every 4 weeks on days 1, 29, and 57. A unique randomization number was assigned via Interactive Web Response System (IWRS) accessed immediately after eligibility confirmation of a patient. The doses selected for this study were supported by the results obtained from previously conducted studies, as well as pharmacokinetic modeling. Patients who had never taken risperidone had a brief trial of oral risperidone 2 mg/day for 3 days during the screening period to ensure lack of any hypersensitivity reactions before the first dose of study drug.

Study Assessments

Efficacy was assessed with the PANSS, CGI-S, and Clinical Global Impression-Improvements (CGI-I) at each scheduled visit. The primary efficacy endpoint was the mean change in PANSS total score from baseline to end of treatment (Day 85 or last post-baseline assessment). The key secondary efficacy endpoint was CGI-S score mean change from baseline to end of treatment. Other secondary efficacy outcomes included mean CGI-I score at endpoint and each post-baseline assessment time point, overall response rate at endpoint (defined as PANSS total score ≥30% decrease from baseline to endpoint or CGI-I score of 2 (much improved) or 1 (very much improved) at endpoint), time to reach overall response, and overall response rate at each post-baseline assessment time point, among others.

Safety was evaluated by assessment of Aes, vital signs, laboratory test, electrocardiograms, physical examinations, ISRs (redness, swelling, and induration), and scales to assess injection site pain (VAS) and extrapyramidal symptoms (AIMS, BARS, and SAS) as well as suicidality (CSSRS).

Statistical Analysis

A sample size of 124 patients in the mITT population in each treatment group would have 90% power to detect a difference in means of nine (standard deviation=20, effect size=0.45) with a 2.5% two-sided significance level for a risperidone group versus the placebo group. The power to show superiority of both risperidone doses to placebo using the above calculation would be at least 81%. Taking into account that each of the two risperidone groups were tested separately against the placebo group, a Bonferroni adjustment for the alfa level was performed. A common standard deviation of 20 in two-group t tests was assumed.

A relatively low post-randomization dropout of 5% rate was anticipated. This assumption was re-assessed at the interim analysis and used in re-estimating the total number of randomized patients required. One unblinded interim analysis was planned to re-estimate the sample size required for the final analysis of up to 558 patients (186 patients per arm) in the mITT population. This interim analysis was to be conducted when ~50% randomized patients, had either reached study day 85 or withdrawn from the study. The decision of the independent Data Monitoring Committee (DMC) was to continue the study without modifying the sample size.

The efficacy analysis was performed on the mITT population containing all randomized patients who received ≥1 dose of study drug with a baseline measurement and ≥1 post-baseline evaluation for the PANSS, and for whom blinding was not potentially compromised (owing to a one-off error in the IWRS).

A mixed effects model with repeated measurements (MMRM) approach was fitted for patients in the mITT population with country where enrolled, visit, treatment, and treatment-by-visit interaction as fixed effects, and baseline PANSS total score as covariate. This MMRM models were used to allow for an unstructured covariance pattern between visits to be fitted, and the visit was fitted in the MMRM as a categorical factor. To utilize the endpoint result (primary outcome) in the MMRM, the endpoint results from any early termination visits were assigned to the next planned protocol visit in the MMRM.

The primary efficacy analysis was supported with sensitivity analyses. All analyses used the Cui, Hung, Wang adjustment, and the Hommel's closed-testing correction procedure to present p values. Confirmatory superiority of each risperidone dose versus placebo was established when p value <0.05. As a sensitivity analysis, the data for the primary endpoint were analyzed for the mITT population using the analysis of covariance (ANCOVA) model.

Point estimates and 95% Cis were obtained using methodology suggested by Hung and Lawrence. This methodology constructs a point estimate and a 95% confidence interval that are motivated by an adaptive test statistic.

The MMRM and ANCOVA models used both observed endpoint values and imputed study day 85 values performed for the mITT population. The ANCOVA models included country and baseline PANSS total score as covariates.

The secondary efficacy endpoints were analyzed using the same model as for the primary efficacy endpoint. Safety and tolerability analyses were performed using data from the safety population, which included all patients who received ≥1 dose of study drug.

An independent DMC monitored patient recruitment, protocol compliance, reviewed safety data, and made recommendations about any existing or potential problems.

Example 11: LAI Depot Compositions (Single Unit Dose Kits)

75 mg Dose

A 75 mg dose of the LAI depot composition comprises the following ingredients in the amounts indicated.

| | Ingredient | Amount (mg) |
|---|---|---|
| Syringe A | PLGA (50:50) having an inherent viscosity of 0.49-0.50 dl/g* | 150 |
| | Risperidone | 75 |
| Syringe B | Dimethyl sulfoxide. | 350 |

*Suitable compositions are made with PLGA (50:50) having an inherent viscosity in the range of 0.20-0.60 dl/g, about 0.30-0.55 dl/g, about 0.36-0.52 dl/g, about 0.40-0.58 dl/g, or about 0.46-0.51 dl/g.

100 mg Dose

A 100 mg dose of the LAI depot composition comprises the following ingredients in the amounts indicated.

| | Ingredient | Amount (mg) |
|---|---|---|
| Syringe A | PLGA (50:50) having an inherent viscosity of 0.48 to 0.50 dl/g | 200 |
| | Risperidone | 100 |
| Syringe B | Dimethyl sulfoxide. | 466.7 |

* Suitable compositions are made with PLGA (50:50) having an inherent viscosity in the range of 0.20-0.60 dl/g, about 0.30-0.55 dl/g, about 0.36-0.52 dl/g, about 0.40-0.58 dl/g, or about 0.46-0.51 dl/g.

Example 12: Clinical Evaluation of LAI Depot Composition

Study Design and Patient Selection

This was a phase III multicenter, randomized, double-blind (DB), placebo controlled clinical trial and an open-label extension (OLE) clinical trial. Participants were aged 18-65 years, with a diagnosis of schizophrenia, according to the diagnostic and Statistical Manual of Mental Disorders, Fifth Edition (DSM-5) criteria. Patients had to be experiencing an acute exacerbation of schizophrenia and had to be hospitalised according to the study protocol, with a Positive and Negative Syndrome Scale (PANSS) score between 80 and 120 (Kay et al., 1987), and a score of ≥4 (moderately ill or worse) on the Clinical Global Impression-Severity scale (CGI-S).

The study design consisted of two phases—a DB phase during which the patients 438 patients were enrolled and randomly assigned in a 1:1:1 ratio to receive monthly LAI depot composition LAI depot composition (75 mg or 100 mg risperidone strength) i.m. (n=145 and n=146, respectively) and placebo (n=147), and an OLE phase lasting up to 52 weeks and designed to determine the efficacy, safety and tolerability in the long-term use of LAI depot composition. To enrich the sample of patients in the OLE phase, together with the patients transitioning the DB phase regardless of the previous treatment (LAI depot composition or placebo), a group of de novo patients previously stabilized with a 4-weeks oral risperidone treatment were admitted. Overall, 215 patients were included in the OLE phase, divided in 3 different groups: stable patients (de novo patients previously treated and stabilized with oral risperidone, n=41), unstable patients (rolling over from the placebo group; n=55) and stabilized patients (rolling over from LAI depot composition; n=119).

Social functioning was assessed by the clinician-administered Personal and Social Performance scale (PSP). The PSP is a 100-point single-item rating scale that is based on 4 areas: personal and social relationships; self-care; socially useful activities, including work, and disturbing and aggressive behaviours. The higher PSP total score indicates a better social functioning. Baseline assessment of PSP occurred before the administration of LAI depot composition on study day 1 (DB phase) or extension study day 1 (OLE phase). For those patients who rolled over from the DB phase, PSP total score at week 12 of the DB phase was used as their baseline for OLE phase.

Health-Related Quality of Life (HRQoL) was assessed through the patient-reported 20-items scale Subjective Well-Being Under Neuroleptics Treatment (SWN-20). The SWN-20 contains 5 different subscales: Mental functioning, Self-control, Emotional regulation, Physical functioning, Social integration, with each subscale score ranging from 4 to 24 and a total score from 20 to 120. To rate this scale, the patients were asked to score identified well-being items as related to antipsychotic treatment on a 6-point scale from "Not at all" to "Very much", with higher scores indicating better HRQoL. This scale has been validated as a reliable measure for subjective well-being in patients with schizophrenia. The SWN-20 was performed as well at all scheduled time-points throughout the whole study duration.

Statistical Analysis

The analysis of both the health-related outcomes was conducted on the intent-to-treat (ITT) population, which consists of all randomized patients who had a baseline measure, received at least 1 dose of study drug, and had ≥1 postbaseline evaluation of PANSS. Since both LAI depot composition 75 and 100 mg showed comparable efficacy results vs placebo, only 2 subgroups were used for DB phase analysis (placebo vs pooled LAI depot composition 75 mg and 100 mg). At baseline, statistical difference between the treatment groups of the summary scores was estimated with a general linear model (GLM) with the summary score as dependent and treatment allocation as independent variables. The GLM has an identity or log link and a normal distribution and gamma distribution was fitted. The best-fitting model parameterization was determined by the Akaike information criterion C statistic. In a second step, the values of these summary scores were summarized (means, 95% Cis) by treatment group over time. P-values for differences between treatment groups over time were estimated with a repeated measurement model which took the interpatient as well as the intra-patient correlation into account. A repeated measurement regression framework considered the repeated measures structure of the data and, if appropriate, additionally allowed regression coefficients to vary across specified subgroups. As mentioned above, the patients who entered OLE phase were divided in 3 different subgroups for the analysis.

At baseline, statistical difference between the treatment groups of the summary scores was estimated with a general linear model (GLM) with the summary score as dependent and treatment allocation as independent variables. The GLM has an identity or log link and a normal distribution and gamma distribution was fitted. The best-fitting model parameterization was determined by the Akaike information criterion C statistic. In a second step, the values of these summary scores were summarized (means, 95% Cis) by treatment group over time. P-values for differences between treatment groups over time were estimated with a repeated measurement model which took the interpatient as well as the intra-patient correlation into account. A repeated measurement regression framework considered the repeated measures structure of the data and, if appropriate, additionally allowed regression coefficients to vary across specified subgroups.

The invention claimed is:

1. A method of treating a subject suffering a relapse of moderate to severe psychosis, the method comprising intramuscularly administering to a subject a LAI depot composition comprising a maintenance dose of 25-150 mg of risperidone suspended in a polymeric solution of DMSO and PLGA copolymer, wherein after said administration an implant formed from said composition provides therapeutic plasma concentrations of total active moiety (risperidone and 9-OH-risperidone) within 2-24 hours after administration and continuously for a period of at least about 28 days, thereby providing significant reduction in symptoms associated with said moderate to severe psychosis as determined by total PANSS (including the positive and negative scales) and CGI-S starting from about 8 days after said administering, wherein said method excludes oral supplementation with risperidone and excludes administration of one or more (plural) loading doses of risperidone in LAI depot composition; and wherein a) said composition is administered intramuscularly once about every 28 days or about once monthly; b) >0 wt % and ≤20% of said risperidone is dissolved in said composition prior to administration; c) the PLGA copolymer has a monomer ratio of lactic acid to glycolic acid in the range from about 50:50 to about 75:25; d) the LAI depot composition has a viscosity in the range of about 0.5-7 Pa·s; e) the LAI depot composition has a mass ratio of DMSO to risperidone of about 5:1 to about 4:1; and f) the LAI depot composition has a mass ratio of risperidone to (PLGA+risperidone), expressed as the percentage of the risperidone weight with respect to total weight of the risperidone plus PLGA, in the range of about 25-35% wt.

2. The method of claim 1, wherein the method provides a) significantly improved PANSS total score (mean difference, 95% CI) from baseline to day 85 of −13.0 (95% CI, −17.3 to −8.8) (p<0.0001) on a placebo-adjusted basis following administration of a maintenance dose of 75 mg of risperidone in a LAI depot composition of the invention; b) significantly improved PANSS total score (mean difference, 95% CI) from baseline to day 85 of −13.3 (−17.6 to −8.9) (p<0.0001) on a placebo-adjusted basis following administration of a maintenance dose of about 100 mg of risperidone in a LAI depot composition of the invention; c) significantly improved CGI-S total score (mean difference, 95% CI) from baseline to day 85 of −0.7 (−1.0 to −0.5) (p<0.0001) on a placebo-adjusted basis following administration of a maintenance dose of about 75 mg of risperidone in a LAI depot composition of the invention; and/or d) significantly improved CGI-S total score (mean difference, 95% CI) from baseline to day 85 of −0.7 (−1.0 to −0.5) (p<0.0001) on a placebo-adjusted basis following administration of a maintenance dose of 100 mg of risperidone in a LAI depot composition of the invention.

3. The method of claim 1, wherein the maintenance dose is about 75-100 mg of risperidone and a) said composition is administered intramuscularly once about every 28 days or about once monthly; b) after said administration, an implant formed from said composition provides a reduction of total PANSS score, in both the positive and negative scales, of −13.3 (−17.6 to −8.9) (p<0.0001) and a reduction of CGI-S total score of −0.7 (−1.0 to −0.5) (p<0.0001), said scores being on a placebo-adjusted basis.

4. A method of improving mental functioning and/or social integration in a human subject experiencing or having recently experienced an episode of acute exacerbation of schizophrenia, the method comprising administering to said subject a long-acting injectable (LAI) depot composition comprising a maintenance dose of 25-150 mg of risperidone suspended in a polymeric solution of DMSO and PLGA copolymer, wherein said composition is administered intramuscularly once about every 28 days or about once monthly, thereby improving mental functioning and/or social integration in said subject as measured using the patient-reported 20-items scale Subjective Well-Being Under Neuroleptics Treatment (SWN-20); and/or improving personal or social relationships, social useful activities, or reducing disturbing and aggressive behaviors, or a combination thereof, in said subject as measured using the Personal and Social Performance (PSP) scale; and wherein a) >0 wt % and >20% of said risperidone is dissolved in said composition prior to administration; b) the PLGA copolymer has a monomer ratio of lactic acid to glycolic acid in the range from about 50:50 to about 75:25; c) the LAI depot composition has a viscosity in the range of about 0.5-7 Pa·s; d) the LAI depot composition has a mass ratio of DMSO to risperidone of about 5:1 to about 4:1; and e) the LAI depot composition has a mass ratio of risperidone to (PLGA+risperidone), expressed as the percentage of the risperidone weight with respect to total weight of the risperidone plus PLGA, in the range of about 25-35% wt.

5. A method of improving mental functioning and/or social integration in a human subject having schizophrenia, wherein said schizophrenia has been previously stabilized by administration of oral risperidone, the method comprising administering to the subject a long-acting injectable (LAI) depot composition comprising a maintenance dose of 25-150 mg of risperidone suspended in a polymeric solution of DMSO and PLGA copolymer, wherein said composition is administered intramuscularly once about every 28 days or about once monthly, thereby improving mental functioning and/or social integration in said subject as measured using the patient-reported 20-items scale Subjective Well-Being Under Neuroleptics Treatment (SWN-20); and/or improving personal or social relationships, social useful activities, or reducing disturbing and aggressive behaviors, or a combination thereof, in said subject as measured using the Personal and Social Performance (PSP) scale; and wherein a) >0 wt % and ≤20% of said risperidone is dissolved in said composition prior to administration; b) the PLGA copolymer has a monomer ratio of lactic acid to glycolic acid in the range from about 50:50 to about 75:25; c) the LAI depot composition has a viscosity in the range of about 0.5-7 Pa·s; d) the LAI depot composition has a mass ratio of DMSO to risperidone of about 5:1 to about 4:1; and e) the LAI depot composition has a mass ratio of risperidone to (PLGA+risperidone), expressed as the percentage of the risperidone weight with respect to total weight of the risperidone plus PLGA, in the range of about 25-35% wt.

6. The method of claim 5, wherein after said administration an implant formed from said composition provides therapeutic plasma concentrations of total active moiety (risperidone and 9-OH-risperidone) within 2-24 hours after administration and continuously for a period of at least about 28 days.

7. The method of claim 6, wherein said maintenance dose comprises a) about 75-100 mg of risperidone; b) about 75 mg of risperidone; or c) about 100 mg of risperidone.

8. The method of claim 1, wherein a) when the subject is administered intramuscularly an initial dose of LAI depot composition comprising about 100 mg of risperidone, the second and subsequent maintenance doses of said composition comprises about 75 mg of risperidone; b) when the subject is administered intramuscularly an initial dose of LAI depot composition comprising about 100 mg of risperidone, the second and subsequent maintenance doses of said composition comprises about 100 mg of risperidone; or c) when the subject is administered intramuscularly an initial dose of LAI depot composition comprising about 75 mg of risperidone, the second and subsequent maintenance doses of said composition comprises about 75 mg of risperidone.

9. The method of claim 1, wherein the method a) excludes the step of administering one or more (plural) loading doses of risperidone in a LAI depot composition before said intramuscular administration of the LAI depot composition; and/or b) excludes the step of orally administering one or more doses of risperidone within said 28-day or monthly period.

10. The method of claim 1, wherein the subject a) is unstable and experiencing severe to moderate psychotic symptoms; b) is experiencing a first acute exacerbation of schizophrenia; c) is undergoing treatment with one or more oral antipsychotic drugs; d) has experienced prior episode(s) of acute exacerbation of schizophrenia; e) is experiencing worsening psychotic symptoms or impending relapse of psychosis; f) is experiencing a relapse of severe to moderate psychotic symptoms; and/or g) is undergoing treatment with a LAI depot composition not according to the invention.

11. The method of claim 1, wherein a) the composition comprises a maintenance dose of about 25 mg to about 125 mg, about 25 mg to about 100 mg, about 50 mg to about 150 mg, about 50 mg to about 125 mg, about 50 mg to about 100 mg, about 75 mg to about 150 mg, about 75 mg to about 125 mg, about 75 mg to about 100 mg, about 25 mg, about 50 mg, about 75 mg, about 100 mg, about 125 mg, or about 150 mg of risperidone; b) the LAI depot composition forms a biodegradable implant in muscle after administration; c) ≤2.5%, ≤5%, ≤7.5%, ≤10%, ≤20% of the risperidone is dissolved in said composition before administration; d) >0%, ≥0.5%, ≥1%, ≥5%, ≥10%, ≥15%, or up to about 20% wt of the risperidone is dissolved in said composition before administration; e) the PLGA copolymer has a monomer ratio of lactic acid to glycolic acid in the range from about 35:65 to about 75:25, about 45:55 to about 70:30, about 50:50 to about 65:35, or about 65:35 to about 75:25, 45:55 to 55:45, or 48:52 to 52:48, or about 50:50, i.e. 50:50±10%, or 75:25±10%; f) before administration, the polymeric solution has a viscosity in the range of about 0.5-7 Pa·s, about 0.5-4 Pa·s, about 0.7-4 Pa·s, about 0.5-3.0 Pa·s, about 0.7-3.0 Pa·s, about 1.5-2.1 Pa·s±10%, about 1.5 to about 2.5 Pa·s, about 1.5 to about 2.3 Pa·s, or about 1.7-1.8 Pa·s±10%; g) the PLGA copolymer has an inherent viscosity in the range of 0.20-0.60 dl/g, about 0.30-0.55 dl/g, about 0.36-0.52 dl/g, about 0.40-0.58 dl/g, or about 0.46-0.51 dl/g measured in chloroform at 30° C. and at a concentration of 0.5% wt with a Ubbelohde size 0 B glass capillary viscometer; h) the LAI depot composition has a mass ratio of DMSO to risperidone of about 4.6:1 to about 4.8:1, about 4.6:1 to about 4.7:1, about 4.67:1, about 4.66:1 or about 4.68:1, or about 4.66:1;

i) the LAI depot composition has a mass ratio of risperidone to (PLGA+risperidone), expressed as the percentage of the risperidone weight with respect to total weight of the risperidone plus PLGA, in the range of about 30-35%, about 31-35%, about 32-34% or about 33% wt; j) the PLGA copolymer is end-capped with an ester group or a carboxyl group; k) the content of risperidone in the formulation is about 10-15% wt, about 11-14% wt, about 12-14% wt, or about 13% wt; l) the PLGA polymer has been irradiated with beta or gamma radiation in the range of 10-30 Kgy, in the range of 15-30 Kgy, or between 16-25 Kgy±10%; m) the composition is sterile; n) the injectable composition continuously provides therapeutically effective plasma levels of total active moiety in the subject throughout a dosing period of at least four weeks beginning from the day of administration; o) before administration, the LAI depot composition has a viscosity in the range of about 1.0-7.0 Pa·s, about 1.5-7.0 Pa·s, or about 1.8-6.5 Pa·s; p) the mass ratio of solvent (DMSO) to polymeric solution, expressed as the weight percentage of solvent with respect to the weight of polymer+solvent, is about 50-75%, about 65-75%, about 60-70%, about 68-72%, or about 70%; q) the concentration of PLGA in the LAI depot composition is in the range of 24%-50% wt, 24%-40% wt, 24%-30% wt, 25-27% wt or 26% wt, (expressed as the percentage of polymer weight based on total composition weight); and/or r) the content of DMSO in the injectable depot composition is about 55-65% wt, about 57-63% wt, about 60-62% wt, or about 61% wt based upon the total weight of the composition.

12. The method of claim 1 further comprising a) providing a container comprising DMSO and a container comprising risperidone and said PLGA copolymer, and mixing the contents of said containers to form said injectable depot composition, then administering said injectable depot composition; or b) providing a container comprising DMSO, a container comprising risperidone, and a container comprising said PLGA copolymer, and mixing the contents of the containers to form said injectable depot composition, then administering said injectable depot composition.

13. The method of claim 12, wherein said containers are included in a kit.

14. The method of claim 13, wherein said kit comprises a single dose of risperidone.

15. The method of claim 4, wherein after said administration an implant formed from said composition provides therapeutic plasma concentrations of total active moiety (risperidone and 9-OH-risperidone) within 2-24 hours after administration and continuously for a period of at least about 28 days.

16. The method of claim 4, wherein a) when the subject is administered intramuscularly an initial dose of LAI depot composition comprising about 100 mg of risperidone, the second and subsequent maintenance doses of said composition comprises about 75 mg of risperidone; b) when the subject is administered intramuscularly an initial dose of LAI depot composition comprising about 100 mg of risperidone, the second and subsequent maintenance doses of said composition comprises about 100 mg of risperidone; or c) when the subject is administered intramuscularly an initial dose of LAI depot composition comprising about 75 mg of risperidone, the second and subsequent maintenance doses of said composition comprises about 75 mg of risperidone.

17. The method of claim 4, wherein the method a) excludes the step of administering one or more loading doses of risperidone in a LAI depot composition before said intramuscular administration of the LAI depot composition;

and/or b) excludes the step of orally administering one or more doses of risperidone within said 28-day or monthly period.

18. The method of claim 4, wherein the subject a) is unstable and experiencing severe to moderate psychotic symptoms; b) is experiencing a first acute exacerbation of schizophrenia; c) is undergoing treatment with one or more oral antipsychotic drugs; d) has experienced prior episode(s) of acute exacerbation of schizophrenia; e) is experiencing worsening psychotic symptoms or impending relapse of psychosis; f) is experiencing a relapse of severe to moderate psychotic symptoms; and/or g) is undergoing treatment with a LAI depot composition not according to the invention.

19. The method of claim 4, wherein a) the composition comprises a maintenance dose of about 25 mg to about 125 mg, about 25 mg to about 100 mg, about 50 mg to about 150 mg, about 50 mg to about 125 mg, about 50 mg to about 100 mg, about 75 mg to about 150 mg, about 75 mg to about 125 mg, about 75 mg to about 100 mg, about 25 mg, about 50 mg, about 75 mg, about 100 mg, about 125 mg, or about 150 mg of risperidone; b) the LAI depot composition forms a biodegradable implant in muscle after administration; c) ≤2.5%, ≤5%, ≤7.5%, ≤10%, ≤20% of the risperidone is dissolved in said composition before administration; d) >0%, ≥0.5%, ≥1%, ≥5%, ≥10%, ≥15%, or up to about 20% wt of the risperidone is dissolved in said composition before administration; e) the PLGA copolymer has a monomer ratio of lactic acid to glycolic acid in the range from about 35:65 to about 75:25, about 45:55 to about 70:30, about 50:50 to about 65:35, or about 65:35 to about 75:25, 45:55 to 55:45, or 48:52 to 52:48, or about 50:50, i.e. 50:50±10%, or 75:25±10%; f) before administration, the polymeric solution has a viscosity in the range of about 0.5-7 Pa·s, about 0.5-4 Pa·s, about 0.7-4 Pa·s, about 0.5-3.0 Pa·s, about 0.7-3.0 Pa·s, about 1.5-2.1 Pa·s±10%, about 1.5 to about 2.5 Pa·s, about 1.5 to about 2.3 Pa·s, or about 1.7-1.8 Pa·s±10%; g) the PLGA copolymer has an inherent viscosity in the range of 0.20-0.60 dl/g, about 0.30-0.55 dl/g, about 0.36-0.52 dl/g, about 0.40-0.58 dl/g, or about 0.46-0.51 dl/g measured in chloroform at 30° C. and at a concentration of 0.5% wt with a Ubbelohde size 0 B glass capillary viscometer; h) the LAI depot composition has a mass ratio of DMSO to risperidone of about 4.6:1 to about 4.8:1, about 4.6:1 to about 4.7:1, about 4.67:1, about 4.66:1 or about 4.68:1, or about 4.66:1; i) the LAI depot composition has a mass ratio of risperidone to (PLGA+risperidone), expressed as the percentage of the risperidone weight with respect to total weight of the risperidone plus PLGA, in the range of about 30-35%, about 31-35%, about 32-34% or about 33% wt; j) the PLGA copolymer is end-capped with an ester group or a carboxyl group; k) the content of risperidone in the formulation is about 10-15% wt, about 11-14% wt, about 12-14% wt, or about 13% wt; l) the PLGA polymer has been irradiated with beta or gamma radiation in the range of 10-30 Kgy, in the range of 15-30 Kgy, or between 16-25 Kgy±10%; m) the composition is sterile; n) the injectable composition continuously provides therapeutically effective plasma levels of total active moiety in the subject throughout a dosing period of at least four weeks beginning from the day of administration; o) before administration, the LAI depot composition has a viscosity in the range of about 1.0-7.0 Pa·s, about 1.5-7.0 Pa·s, or about 1.8-6.5 Pa·s; p) the mass ratio of solvent (DMSO) to polymeric solution, expressed as the weight percentage of solvent with respect to the weight of polymer+solvent, is about 50-75%, about 65-75%, about 60-70%, about 68-72%, or about 70%; q) the concentration of PLGA in the LAI depot composition is in the range of 24%-50% wt, 24%-40% wt, 24%-30% wt, 25-27% wt or 26% wt, (expressed as the percentage of polymer weight based on total composition weight); and/or r) the content of DMSO in the injectable depot composition is about 55-65% wt, about 57-63% wt, about 60-62% wt, or about 61% wt based upon the total weight of the composition.

20. The method of claim 5, wherein a) when the subject is administered intramuscularly an initial dose of LAI depot composition comprising about 100 mg of risperidone, the second and subsequent maintenance doses of said composition comprises about 75 mg of risperidone; b) when the subject is administered intramuscularly an initial dose of LAI depot composition comprising about 100 mg of risperidone, the second and subsequent maintenance doses of said composition comprises about 100 mg of risperidone; or c) when the subject is administered intramuscularly an initial dose of LAI depot composition comprising about 75 mg of risperidone, the second and subsequent maintenance doses of said composition comprises about 75 mg of risperidone.

21. The method of claim 5, wherein the method excludes the step of orally administering one or more doses of risperidone within said 28-day or monthly period.

22. The method of claim 5, wherein the subject a) is experiencing severe to moderate psychotic symptoms; b) is experiencing a first acute exacerbation of schizophrenia; c) is undergoing treatment with one or more oral antipsychotic drugs; d) has experienced prior episode(s) of acute exacerbation of schizophrenia; e) is experiencing worsening psychotic symptoms or impending relapse of psychosis; f) is experiencing a relapse of severe to moderate psychotic symptoms; and/or g) is undergoing treatment with a LAI depot composition not according to the invention.

23. The method of claim 5, wherein a) the composition comprises a maintenance dose of about 25 mg to about 125 mg, about 25 mg to about 100 mg, about 50 mg to about 150 mg, about 50 mg to about 125 mg, about 50 mg to about 100 mg, about 75 mg to about 150 mg, about 75 mg to about 125 mg, about 75 mg to about 100 mg, about 25 mg, about 50 mg, about 75 mg, about 100 mg, about 125 mg, or about 150 mg of risperidone; b) the LAI depot composition forms a biodegradable implant in muscle after administration; c) ≤2.5%, ≤5%, ≤7.5%, ≤10%, ≤20% of the risperidone is dissolved in said composition before administration; d) >0%, ≥0.5%, ≥1%, ≥5%, ≥10%, ≥15%, or up to about 20% wt of the risperidone is dissolved in said composition before administration; e) the PLGA copolymer has a monomer ratio of lactic acid to glycolic acid in the range from about 35:65 to about 75:25, about 45:55 to about 70:30, about 50:50 to about 65:35, or about 65:35 to about 75:25, 45:55 to 55:45, or 48:52 to 52:48, or about 50:50, i.e. 50:50±10%, or 75:25±10%; f) before administration, the polymeric solution has a viscosity in the range of about 0.5-7 Pa·s, about 0.5-4 Pa·s, about 0.7-4 Pa·s, about 0.5-3.0 Pa·s, about 0.7-3.0 Pa·s, about 1.5-2.1 Pa·s±10%, about 1.5 to about 2.5 Pa·s, about 1.5 to about 2.3 Pa·s, or about 1.7-1.8 Pa·s±10%; g) the PLGA copolymer has an inherent viscosity in the range of 0.20-0.60 dl/g, about 0.30-0.55 dl/g, about 0.36-0.52 dl/g, about 0.40-0.58 dl/g, or about 0.46-0.51 dl/g measured in chloroform at 30° C. and at a concentration of 0.5% wt with a Ubbelohde size 0B glass capillary viscometer; h) the LAI depot composition has a mass ratio of DMSO to risperidone of about 4.6:1 to about 4.8:1, about 4.6:1 to about 4.7:1, about 4.67:1, about 4.66:1 or about 4.68:1, or about 4.66:1; i) the LAI depot composition has a mass ratio of risperidone to (PLGA+risperidone), expressed as the percentage of the risperidone weight with respect to total weight of the risperidone plus PLGA, in the range of about 30-35%, about 31-35%, about 32-34% or about 33% wt; j) the PLGA copolymer is end-capped with an ester group or a carboxyl group; k) the content of risperidone in the formulation is about 10-15% wt, about 11-14% wt, about 12-14% wt, or about 13% wt; l) the PLGA polymer has been irradiated with beta or gamma radiation in the range of 10-30 Kgy, in the range of 15-30 Kgy, or between 16-25 Kgy±10%; m) the composition is sterile; n) the injectable composition continuously provides therapeutically effective plasma levels of total active moiety in the subject throughout a dosing period of at least four weeks beginning from the day of administration; o) before administration, the LAI depot composition has a viscosity in the range of about 1.0-7.0 Pa·s, about 1.5-7.0 Pa·s, or about 1.8-6.5 Pa·s; p) the mass ratio of solvent (DMSO) to polymeric solution, expressed as the weight percentage of solvent with respect to the weight of polymer+solvent, is about 50-75%, about 65-75%, about 60-70%, about 68-72%, or about 70%; q) the concentration of PLGA in the LAI depot composition is in the range of 24%-50% wt, 24%-40% wt, 24%-30% wt, 25-27% wt or 26% wt, (expressed as the percentage of polymer weight based on total composition weight); and/or r) the content of DMSO in the injectable depot composition is about 55-65% wt, about 57-63% wt, about 60-62% wt, or about 61% wt based upon the total weight of the composition.

* * * * *